US012807639B2

(12) United States Patent
Pochapsky et al.

(10) Patent No.: US 12,807,639 B2
(45) Date of Patent: Nov. 24, 2026

(54) SELECTIVE ISONITRILE INHIBITORS OF CYTOCHROME P450 SUBTYPES

(71) Applicant: Brandeis University, Waltham, MA (US)

(72) Inventors: Thomas Charles Pochapsky, Arlington, MA (US); Nathan Ross Wong, Salem, MA (US); Reethy Sundar, Lexington, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 309 days.

(21) Appl. No.: 18/686,734

(22) PCT Filed: Aug. 25, 2022

(86) PCT No.: PCT/US2022/041487

§ 371 (c)(1),
(2) Date: Feb. 26, 2024

(87) PCT Pub. No.: WO2023/028205

PCT Pub. Date: Mar. 2, 2023

(65) Prior Publication Data

US 2024/0368212 A1 Nov. 7, 2024

Related U.S. Application Data

(60) Provisional application No. 63/237,421, filed on Aug. 26, 2021.

(51) Int. Cl.

| | |
|---|---|
| ***A61K 31/56*** | (2006.01) |
| ***A61K 31/57*** | (2006.01) |
| ***A61K 45/06*** | (2006.01) |
| ***A61K 47/69*** | (2017.01) |
| ***C07J 41/00*** | (2006.01) |

(52) U.S. Cl.

CPC .......... *C07J 41/0094* (2013.01); *A61K 31/56* (2013.01); *A61K 31/57* (2013.01); *A61K 45/06* (2013.01); *A61K 47/6929* (2017.08)

(58) Field of Classification Search

CPC .. C07J 41/0094; A61K 47/6929; A61K 31/56; A61K 31/57; A61K 45/06

See application file for complete search history.

(56) References Cited

U.S. PATENT DOCUMENTS

| | | | |
|---|---|---|---|
| 3,705,179 | A | 12/1972 | Marshall et al. |
| 4,501,701 | A | 2/1985 | Barton et al. |
| 4,647,410 | A | 3/1987 | Van, Leusen et al. |
| 7,482,334 | B2 | 1/2009 | Fringke et al. |
| 9,115,168 | B2 | 8/2015 | Fringke |
| 9,518,080 | B2 | 12/2016 | Runyon et al. |
| 10,137,137 | B2 | 11/2018 | Marsault et al. |
| 10,993,949 | B2 | 5/2021 | Gerloni |
| 2014/0162942 | A1 | 6/2014 | Ghosal et al. |
| 2016/0243247 | A1 | 8/2016 | Bradner et al. |
| 2019/0247402 | A1 * | 8/2019 | Reddy ..................... A61P 25/20 |
| 2020/0078346 | A1 | 3/2020 | Parkinson |

OTHER PUBLICATIONS

Alaina, M. et al.; "Steroid-Derived Isonitriles are Potent Cytochrome P450 Ligands that Should Enable Solution NMR as a Structural Technique to Probe 450 Dynamics"; The Faseb Journal, vol. 36, Supp 1, Abs R5823; DOI:10.1096/fasebj.2022.36.S1.R5823 (2022).

Devore, NM. et al.; "Key Residues Controlling Binding of Diverse Ligands to Human Cytochrome P450 2A Enzymes"; Drug Metabolism and Disposition, vol. 37, Issue No. 6; pp. 1319-1327; DOI:10.1124/dmd.109.026765 (2009).

European Search Report for European Application 22862064.7 [PCT/US2022/041487] dated Nov. 2, 2026; 20 pages.

Evans, et al.; "Isocyanides Inhibit Human Heme Oxygenases at the Verdoheme Stage"; Biochemistry, vol. 48, Issue No. 37; pp. 8920-8928; DOI:10.1021/bi9011258 (2009).

Galli, U. et al.; "Metabolic Fate of the Isocyanide Moiety: Are Isocyanides Pharmacophore Groups Neglected by Medicinal Chemists?"; Chem Res Toxicol, vol. 33, Issue No. 4; pp. 955-966; DOI:10.1021/acs.chemrestox.9b00504 (2020).

Giner and Djerassi; "Inhibition and Substrate Specificity of Yeast Delta-22—Desaturase"; Biochem Biophys Res Comm, vol. 173, Issue No. 1; pp. 60-66; DOI:10.1016/S0006-291X(05)81021-6 (1990).

Harris, et al.; "Structural and Biochemical Characterization of CYP2D6-Mediated Dextromethorphan Metabolism Using Isonitrile-based Analogs"; ASPET 2024 Annual Meeting, Abstract; DOI:10.1124/jpet.234.972290 (2024).

Hertler and Corey; "A Novel Preparation of Isonitriles";J Org Chem, vol. 23, Issue No. 1; pp. 1221-1222: DOI:10.1021/jo01102a612?ref=article_openPDF (1958).

Horobin, R.W. et al.; "Stereoselective thermal isomerization of steroidal isocyanides to cyanides"; Tetrahedron Letters, vol. 42; pp. 5087-5089 (1966).

International Search Report and Written Opinion for International Application PCT/US2024/055242; International Filing Date: Nov. 8, 2024; Date of Mailing; Feb. 26, 2025; 10 pages.

Lamb et al.; "Biodiversity of the P450 catalytic cycle: yeast cytochrome b"5/NADH cytochrome b"5 reductase complex efficiently drives the entire sterol 14-demethylation (CYP51) reaction"; FEBS Letters 462(3) pp. 283-288 (1999).

(Continued)

*Primary Examiner* — Timothy R Rozof

(74) *Attorney, Agent, or Firm* — CANTOR COLBURN LLP

(57) ABSTRACT

Described herein are steroid or steroid-like compounds including at least one isonitrile group and which inhibit the activity of a cytochrome P450 enzyme, as well as compositions including the compounds. Also included are methods of inhibiting activity of a cytochrome P450 in a subject having a steroid-responsive cancer, a *Mycobacterium tuberculosis* infection, a fungal infection, or a trypanosome infection, the method comprising administering to the subject the compound including at least one isonitrile group or a pharmaceutically acceptable salt thereof, in an amount effective to inhibit the CYP activity in the subject.

23 Claims, 13 Drawing Sheets

(56) References Cited

OTHER PUBLICATIONS

Massarotti, A. et al.; "Medicinal Chemistry of Isocyanides"; Chem Rev, vol. 121, Issue No. 17; pp. 10742-10788; DOI:10.1021/acs.chemrev.1c00143 (2021).
Nadaria, N. et al.; "Steroids. LIV. Synthesis of 17[beta]-amino-5[alpha]-androstan-3[alpha]-ol from epiandrosterone"; Database Hcaplus, Database Accession No. 110: 24130 (from Zh Org Khim, vol. 24, Issue No. 4; pp. 760-765) (1988).
Paulekuhn, G. et al.; "Trends in Active Pharmaceutical Ingredient Salt Selection based on Analysis of the Orange Book Database"; Journal of Medicinal Chemistry, vol. 50, Issue No. 26; pp. 6665-6672; DOI:10.1021/jm701032y (2007).
Singh, C. et al.; "In vivo active antimalarial isonitriles"; Bioorg Med Chem Letters, vol. 12, Issue No. 17; pp. 2277-2279; DOI:10.1016/S0960-894X(02)00457-2 (2002).
International Search Report of the ISA/US mailed Jan. 18, 2023 for International Application No. PCT/US2022/041487 filed Aug. 25, 2022, 5 pages.
Johnston, Jonathan B. et al. "Substrate analog studies of the ω-regiospecificity of Mycobacterium tuberculosis cholesterol metabolizing cytochrom P450 enzymes CYP124A1, CYP125A1 and CYP142A1", Bioorganic & Medicinal Chemistry 20 (2012) pp. 4064-4081.
Lee, D-S. et al.; "Structural Characterization of n-Butyl-isocyanide Complexes of Cytochromes P450nor and P450cam"; Biochemistry, vol. 40, Issue No. 9; 2001; pp. 2669-2677.
PubChem Compound Summary. [(3Z, 10S, 13S, 17S)-17-(1-hydroxy-1-isocyanoethyl)-10, 13-dimethyl-2,3,4,5,6,7,8,9,11,12,14,15,16,17-tetradecahydro-1H-cyclopenta[a]phenanthren-3-yl] acetate. Rev. Jan. 21, 2023. 8 pages.
Written Opinion of the ISA/US mailed Jan. 18, 2023 for International Application No. PCT/US2022/041487 filed Aug. 25, 2022, 7 pages.

* cited by examiner

SELECTIVE ISONITRILE INHIBITORS OF CYTOCHROME P450 SUBTYPES

CROSS REFERENCE TO RELATED APPLICATIONS

This application is a National Stage application of PCT/US2022/041487 filed Aug. 25, 2022, which claims the benefit of U.S. Provisional Application No. 63/237,421 filed August 26, 202, both of which are incorporated by reference in their entirety herein.

FEDERAL RESEARCH STATEMENT

This invention was made with government support under grant number R01GM130997 awarded by the National Institutes of Health. The government has certain rights in the invention.

BACKGROUND

Cytochromes P450 (CYPs) are a diverse superfamily of heme-containing monooxygenase enzymes that use $O_2$ to oxidize organic molecules, often in a highly selective manner. Over 600,000 CYP genes have been identified in organisms from all kingdoms and phyla of life. There are 57 different CYP genes in humans which encode CYPs involved in steroid hormone and prostaglandin biosynthesis, drug activation and metabolism. Not surprisingly, CYP enzymes play an important role in pharmacology. Many antifungal drugs (e.g., ketoconazole and related azoles) act by inhibiting CYP51A1. Cancer chemotherapy regimens, particularly of steroid-responsive cancers, often involve inhibition of a CYP.

Equally important is the role of CYPs in drug activation and metabolism. Drug candidates are routinely screened against panels of CYPs in order to establish metabolic profiles and drug tolerability. The metabolic profile reflects whether a drug candidate is metabolized too slowly or too quickly and which CYP is responsible for its metabolism. For example, one of the most important CYPs for drug metabolism, CYP3A4, is involved in the detoxification and removal of approximately 50% of all small-molecule drugs currently available. The ability of HIV-suppressing drug "cocktails" to retain activity for extended times depend on the presence of cobicistat, a CYP3A4-suppressing component. The warnings on many drug labels that grapefruit juice not be taken with the drug is due to the presence of bergamottin, which upon oxidation by CYP3A4 and other CYPs irreversibly inactivates the enzymes.

The majority of drugs that act via inhibition of CYPs work by the same mechanism, the binding of a nitrogen heterocycle (imidazole or pyridine) to the oxidized ($Fe^{3+}$) of the heme via a Fe—N dative covalent bond (FIG. 1A). These "type II" inhibitors vary in the organic framework to which the heterocycle is attached. There are two major drawbacks with this type of inhibition. First, P450 enzymes function by cycling between the $Fe^{3+}$ and $Fe^{2+}$ oxidation states, and type II inhibitors only bind tightly to the $Fe^{3+}$ state, so there is the possibility that reduction of the Fe will break the Fe—N bond, allowing the inhibitor to escape the active site. An additional drawback is that of cross-inhibition, that is, a molecule that inhibits one CYP is likely to inhibit others to some extent, making off-target effects likely.

Thus there remains a need for CYP inhibitors having improved CYP selectivity as reduced dependence on the oxidation state of the iron in the heme group of the CYP molecule.

SUMMARY

Disclosed herein is a compound represented by Formula 1 and comprising at least one isonitrile (—NC), or a pharmaceutically acceptable salt thereof (Formula 1)

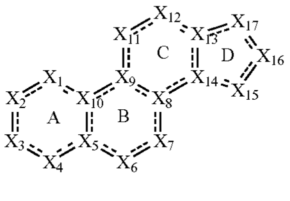

wherein $X_1$ is N, $N(R_{11})$, $C(R_{11})$, O, S, S(=O), C(=Y), $C(=N—OR_{11})$, $C(R_{11})(R_{12})$, or L(N≡C);

$X_2$ is N, $N(R_{21})$, $C(R_{21})$, O, S, S(=O), C(=Y), $C(=N—OR_{21})$, $C(R_{21})(R_{22})$, or L(N≡C);

$X_3$ is N, $N(R_{31})$, $C(R_{31})$, O, S, S(=O), C(=Y), $C(=N—OR_{31})$, $C(R_{31})(R_{32})$, or L(N≡C);

$X_4$ is N, $N(R_{41})$, $C(R_{41})$, O, S, S(=O), C(=Y), $C(=N—OR_{41})$, $C(R_{41})(R_{42})$, or L(N≡C);

$X_5$ is C, N, S, $C(R_{51})$, or L(N≡C);

$X_6$ is N, $N(R_{61})$, $C(R_{61})$, O, S, S(=O), C(=Y), $C(=N—OR_{61})$, $C(R_{61})(R_{62})$, or L(N≡C);

$X_7$ is N, $N(R_{71})$, $C(R_{71})$, O, S, S(=O), C(=Y), $C(=N—OR_{71})$, $C(R_{71})(R_{72})$, or L(N≡C);

$X_8$ is C, N, S, $C(R_{81})$, or L(N≡C);

$X_9$ is C, N, S, $C(R_{91})$, or L(N≡C);

$X_{10}$ is C, N, S, $C(R_{101})$, or L(N≡C);

$X_{11}$ is N, $N(R_{111})$, $C(R_{111})$, O, S, S(=O), C(=Y), $C(=N—OR_{111})$, $C(R_{111})(R_{112})$, or L(N≡C);

$X_{12}$ is N, $N(R_{121})$, $C(R_{121})$, O, S, S(=O), C(=Y), $C(=N—OR_{121})$, $C(R_{121})(R_{122})$, or L(N≡C);

$X_{13}$ is C, N, S, $C(R_{131})$, or L(N≡C);

$X_{14}$ is C, N, S, $C(R_{141})$, or L(N≡C);

$X_{15}$ is N, $N(R_{151})$, $C(R_{151})$, O, S, S(=O), C(=Y), $C(=N—OR_{151})$, $C(R_{151})(R_{152})$ or L(N≡C);

$X_{16}$ is N, $N(R_{161})$, $C(R_{161})$, O, S, S(=O), C(=Y), $C(=N—OR_{161})$, $C(R_{161})(R_{162})$ or L(N≡C);

$X_{17}$ is N, $N(R_{171})$, $C(R_{171})$, O, S, S(=O), C(=Y), $C(=N—OR_{171})$, $C(R_{171})(R_{172})$ or L(N≡C);

Y is N, O, S, or $C_1$-$C_{12}$ alkyl in which any carbon-carbon single bond is optionally replaced by a carbon-carbon double or triple bond, any methylene is optionally replaced by O, S, or $NR^{10}$, and optionally substituted with one or more substituents independently chosen from halogen, hydroxyl, cyano, amino, and oxo;

$R_{10}$, $R_{11}$, $R_{12}$, $R_{21}$, $R_{22}$, $R_{31}$, $R_{32}$, $R_{41}$, $R_{42}$, $R_{51}$, $R_{61}$, $R_{62}$, $R_{71}$, $R_{81}$, $R_{91}$, $R_{101}$, $R_{111}$, $R_{112}$, $R_{121}$, $R_{122}$, $R_{131}$, $R_{141}$, $R_{151}$, $R_{152}$, $R_{161}$, $R_{162}$, $R_{171}$, and $R_{172}$ are each independently hydrogen, deuterium, hydroxyl, halogen, $C_1$-$C_{12}$ alkyl in which any carbon-carbon single bond is optionally replaced by a carbon-carbon double or triple bond, any methylene is optionally replaced by O, S, Si, Ge, P, or $NR^{10}$, and optionally substituted with one or more substituents independently chosen from halogen, hydroxyl, cyano, amino, and oxo;

L is a single bond or a $C_1$-$C_{12}$ alkyl in which any carbon-carbon single bond is optionally replaced by a carbon-carbon double or triple bond, any methylene is optionally replaced by O, S, Si, Ge, P, or $NR^{10}$, and optionally substituted with one or more substituents independently chosen from halogen, hydroxyl, cyano, amino, and oxo;

optionally, any two adjacent substituents may form a $C_5$-$C_7$ carbocyclic ring or a $C_2$-$C_7$ heterocyclic ring;

optionally, any two substituents on the same carbon may form a carbocyclic or heterocyclic spiro ring system with any of rings A-D; and ══════ represents a single or a double bond provided that rings A, B, C, and D are not simultaneously aromatic.

Also disclosed are pharmaceutical compositions comprising the disclosed compounds or a pharmaceutically acceptable salt thereof, and a pharmaceutically acceptable carrier.

In an aspect, a composition comprises a plurality of encapsulated nanoparticles, wherein each of the nanoparticles independently comprises a core comprising a disclosed compound or a pharmaceutically acceptable salt thereof, and an outer shell at least partially encapsulating the core.

In another aspect, a method of inhibiting activity of a cytochrome P450 (CYP) in a subject having a steroid-responsive cancer, an antibiotic-resistant *Mycobacterium tuberculosis* infection, a fungal infection, or a trypanosome infection, comprises administering to the subject a disclosed compound or a pharmaceutically acceptable salt thereof, in an amount effective to inhibit the CYP activity in the subject.

In an aspect, a method of treating a steroid-responsive cancer in a subject comprising administering to the subject a disclosed compound or a pharmaceutically acceptable salt thereof, in an amount effective to treat the steroid-responsive cancer in the subject.

In an aspect, a method of treating a *Mycobacterium tuberculosis* infection in a subject comprising administering to the subject a disclosed compound or a pharmaceutically acceptable salt thereof, in an amount effective to treat the *Mycobacterium tuberculosis* infection in the subject.

In an aspect, a method of treating a fungal infection in a subject comprising administering to the subject a disclosed compound or a pharmaceutically acceptable salt thereof, in an amount effective to treat or prevent the fungal infection in the subject.

The above described and other features are exemplified by the following figures and detailed description.

BRIEF DESCRIPTION OF THE DRAWINGS

The following figures are exemplary embodiments wherein the like elements are numbered alike.

FIG. 2A shows substantially linear arrangement of Fe—C—N—R in an exemplary embodiment. FIG. 2B shows an exemplary embodiment where the bond between Fe and C is weakened when a non-linear arrangement is present.

FIG. 3A shows the optical difference spectrum for the titration of CYP17A1 (0.2 μM) with isonitrile compound 16 (concentrations range from 0 μM to 0.2 μM in approximately 0.015 μM increments). The maximum absorbance was at 430 nm and the trough was at 393 nm. FIG. 3B shows the optical difference spectrum for the titration of CYP106A2 (1.0 μM) with isonitrile compound 17 (concentrations range from 0 μM to 20 μM in approximately 0.015 μM increments). The trough was at 418 nm. FIG. 3C shows the titration of CYP106A2 (1.0 μM) with isonitrile compound 19 (concentrations range from 0 μM to 10 μM in approximately 1 μM increments). Neither compound shows cross-reactivity with the other CYP.

FIG. 5A shows a plot of the absorbance changes due to titration of CYP17A1 with 16 (white circles) and abiraterone (black circles) reveal that both compounds bind very tightly. FIG. 5B shows that CYP17A1 progesterone hydroxylation is inhibited by both compounds, but more potently by abiraterone (black circles) than by 16 (white circles).

FIGS. 7A-7C show the binding of 20-(R)-16 to human drug-metabolizing cytochrome P450 enzymes. FIG. 7A shows the optical difference spectrum showing titration of CYP3A4 (1.0 μM) with of 20-(R)- (concentrations range from 0 μM to 20 μM in approximately 0.015 μM increments)] also yields the difference spectrum peak at 430 nm indicative of Fe—CN bond formation. FIG. 7B shows a plot of absorbance changes vs. ligand concentration reveals $K_d$ values of approximately 300 nM and 250 nM for CYP3A4 (circles, n=3, 95% CI 260-330 nM) and CYP2D6 (triangles, n=2, 95% CI 210-280 nM), respectively. Both CYP3A4 and CYP2D6 were each present at a concentration 0f 1.0 μM.

FIG. 9A shows the CYP17A1/20-(R)-16 complex after reduction by sodium dithionite, yielding a split Soret with maxima at 430 and 455 nm. The sample includes CYP17A1 at a concentration of 1.0 μM, saturated with 20-(R)-16 at a concentration of 2.0 μM. FIG. 9B shows the CYP3A4/20-(R)-16 complex after reduction by sodium dithionite, also yielding a split Soret with maxima at 426 and 455 nm (time zero), which slowly re-oxidizes to the original 435 nm (after 103 min) upon air exposure. The sample includes CYP3A4 at a concentration of 1.0 μM, saturated with 20-(R)-16 at a concentration of 5.0 μM.

DETAILED DESCRIPTION

Disclosed herein are isonitrile-containing compounds derived from steroids or steroid-like compounds and which are designed to selectively inhibit various cytochrome P450s (CYPs) that oxidize steroids and steroid-like compounds. The isonitrile-containing compounds can be derived from known steroid or steroid-like compounds or from those compounds considered likely to act as inhibitors based on the substrate preferences and regioselectivity and stereoselectivity of oxidations catalyzed by a particular CYP. The resulting isonitrile-containing inhibitors exhibit high affinity for the target CYP, with low cross-reactivity with non-target CYPs.

Figure 1A:
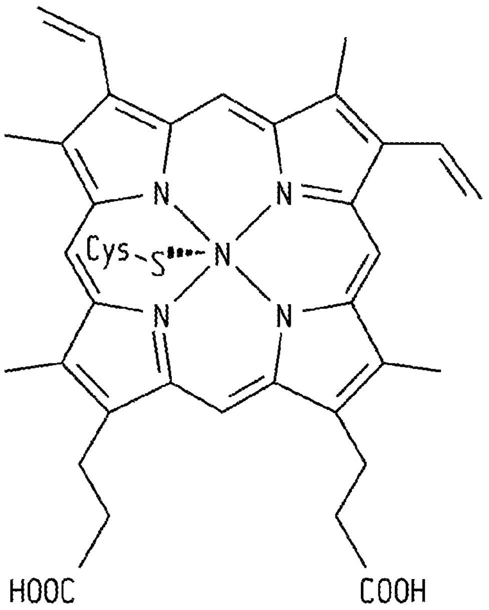
FIG. 1A shows the heme cofactor of CYPs, with conserved axial cysteinyl sulfur ligand.
Figure 1B:
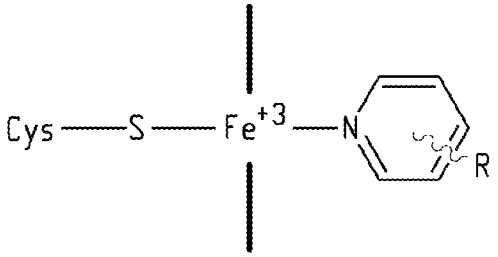
FIG. 1B is an illustration of type II inhibition by a substituted pyridine, with the heme viewed edge on represented by heavy black lines.
Figure 1C:
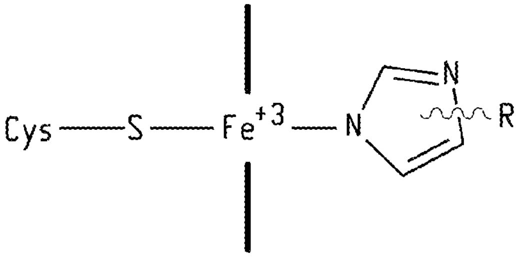
FIG. 1C is an illustration of type II inhibition by a substituted imidazole. The position and nature of the R substituent on both the imidazole and pyridine rings varies depending on the inhibitor. Note that the inhibitor is free to rotate around the Fe—N bond, so multiple positions of R can be accommodated.
Figure 2A:
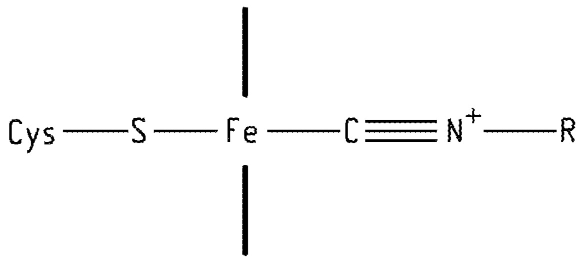
FIGS. 2A and 2B are illustrations of isonitrile binding to CYP heme iron.
Figure 2B:
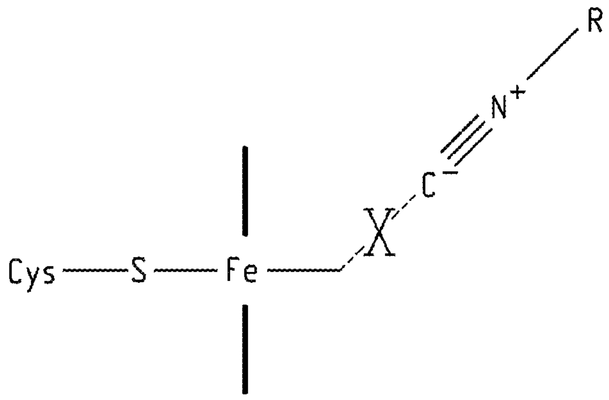

Organic isonitrile-containing compounds are capable of inhibiting CYPs with both an improved selectivity for particular targeted CYPs and reduced dependence on the oxidation state of the iron. The isonitrile functional group (—NC), is a commonly used and readily prepared intermediate in organic syntheses. The isonitrile functionality shows some similarity in metal binding to carbon monoxide (CO). The poisonous nature of CO is due to the fact that it binds in place of $O_2$ to the heme $Fe^{2+}$ in hemoglobin. CO binds to CYPs in a similar fashion in their $Fe^{2+}$ form, giving rise to an absorption spectrum maximum at 450 nm, from which the name cytochrome P450 is derived. Organic isonitriles (e.g., methyl or butyl isonitrile) can bind to CYPs in a manner similar to CO, but unlike CO, isonitriles do not require the heme iron to be reduced in order to bind, but will instead bind readily to the $Fe^{3+}$ form as well (see FIG. 2). Without being limited by theory, because isonitrile binding to the heme in cytochrome P450 is strongest when the Fe—C—N—R atoms are arranged in a substantially linear fashion, the binding of isonitriles is expected to be more sterically stringent than for type II inhibitors, which can rotate around the Fe—N bond so as to best accommodate the organic functionality to which the imidazole/pyridine is appended. The steric restraints imparted by the isonitrile group are not present for other type II binders. As such, isonitrile-type inhibitors are more selective, as the position of the appended functionality R in the enzyme active site will be restricted relative to those in the type II inhibitors.

It has been advantageously discovered that isonitrile-containing compounds derived from steroid or steroid-like compounds, or from those compounds considered likely to act as inhibitors based on the substrate preferences of particular CYPs, selectively bind to a specific cytochrome P450 while having low cross-reactivity with others. In addition, the use of an oxidation product of a given cytochrome P450 to determine where to derivatize the steroid or steroid-like compound has also been discovered.

The compositions, methods, and articles disclosed herein can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity and are to be construed to cover both the singular and the plural, unless otherwise indicated herein or clearly contradicted by context. "Or" means "and/or" unless clearly stated otherwise. Reference throughout the specification to "an embodiment" or "an aspect" means that a particular element described in connection with the embodiment or aspect is included in at least one embodiment or aspect described herein, and may or may not be present in other embodiments or aspects. In addition, it is to be understood that the described elements may be combined in any suitable manner in the various embodiments. A "combination thereof" is open and includes any combination comprising at least one of the listed components or properties optionally together with a like or equivalent component or property not listed Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds of Formula I include all compounds of Formula I having isotopic substitutions at any position. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "Formula I" encompasses all compounds that satisfy Formula I, including any enantiomers, racemates and stereoisomers, as well as all pharmaceutically acceptable salts, solvates, and hydrates of such compounds. For example, when "Formula I" includes substituents on the rings, both the α and β isomers are encompassed by "Formula I". In addition, when "Formula I" includes a substituent having a chiral center, then all stereoisomers (e.g., R or S) are encompassed by "Formula I." "Formula I" includes all subgeneric groups of Formula I unless clearly contraindicated by the context in which this phrase is used.

"Cytochrome P450" or "CYP" refer to a superfamily of heme-containing monooxygenase enzymes that activate $O_2$ for oxidizing organic molecules such as steroids, fatty acids, and xenobiotics, and which are involved in metabolism of various compounds, often in a highly selective manner.

"Treatment" or "treating" means providing the active agent (compound) disclosed herein as either the only active agent or together with at least one additional active agent sufficient to: (a) inhibit activity of a cytochrome P450 in a subject; (b) inhibit a cancer (i.e., arrest its development) or cause regression of the cancer; or (c) inhibit the development of a disease or relieve a disease caused by a *Mycobacterium tuberculosis* infection, a fungal infection, or a trypanosome infection. In certain circumstances a patient may not present symptoms of a condition for which the patient is being treated.

"Prevention" or "preventing" as used herein includes (1) avoid the development of a disease in a subject at risk for the disease or (2) effecting a significant delay in the onset of symptoms of the disease in a subject at risk of developing symptomatic disease beyond the time when subject is predicted to develop symptomatic disease if untreated. A method of prevention usually starts before the obvious sickness of the disease.

An "effective amount" or "therapeutically effective amount" of an active agent or a composition including the active agent means an amount effective, when administered to a subject, to provide a therapeutic benefit. The therapeutic benefit can include an amelioration of symptoms, a decrease in disease progression, or inhibiting the development of the disease. An effective amount can vary depending upon a variety of factors including the age, body weight, general health, sex, diet, time of administration, route of administration, rate of excretion, drug combination, and the severity of the particular disorder for the patient undergoing therapy. Thus, it is not always possible to specify an exact "effective amount." However, an appropriate "effective" amount in any individual case may be determined by one of ordinary skill in the art using routine experimentation. A therapeutically effective amount of an active agent may also be an amount sufficient to provide a significant positive effect on any indicium of a disease, disorder, or condition. A significant effect on an indicium of a disease, disorder, or condition is statistically significant in a standard parametric test of statistical significance, for example Student's T-test, where $p \leq 0.05$.

"Providing" means giving, administering, selling, distributing, transferring (for profit or not), manufacturing, compounding, or dispensing.

"Administering" means giving, providing, applying, or dispensing by any suitable route. Administration of a combination of active agents includes administration of the combination in a single formulation or unit dosage form, administration of the individual active agents of the combination concurrently but separately, or administration of the individual active agents of the combination sequentially by any suitable route. The dosage of the individual active agents of the combination may require more frequent administration of one of the active agent(s) as compared to the other active agent(s) in the combination. Therefore, to permit appropriate dosing, packaged pharmaceutical products may contain one or more dosage forms that contain the combination of active agents, and one or more dosage forms that contain one of the combination of active agents, but not the other active agent(s) of the combination.

"Pharmaceutical compositions" are compositions comprising an active agent, and at least one other substance, such as an excipient. An excipient can be a carrier, filler, diluent, bulking agent or other inactive or inert ingredients. Pharmaceutical compositions optionally contain one or more additional active agents. When specified, pharmaceutical compositions meet the U.S. FDA's GMP (good manufacturing practice) standards for human or non-human drugs.

"Pharmaceutically-acceptable carrier" refers to a diluent, adjuvant, excipient, or carrier, other ingredient, or combination of ingredients that alone or together provide a carrier or vehicle with which a compound or compounds of the invention is formulated and/or administered, and in which every ingredient or the carrier as a whole is pharmaceutically) acceptable. Also included are any and all solvents, dispersion media, coatings, antibacterial and antifungal agents, and isotonic and absorption delaying agents. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "combination therapy" refers to the administration of two or more therapeutic (active) agents to treat a therapeutic condition or disorder described in the present disclosure. Such administration encompasses co-administration of these therapeutic agents in a substantially simultaneous manner, such as in a single dosage form having a fixed ratio of active ingredients or in separate dosage forms for each active ingredient. In addition, such administration also encompasses administration of each therapeutic agent in a sequential manner, either at approximately the same time or at different times. In either case, the treatment regimen will provide the beneficial effects of each therapeutic agent in the drug combination in treating the conditions or disorders described herein.

A "patient" or a "subject" means a human or non-human animal in need of medical treatment. Medical treatment can include treatment of an existing condition, such as a disease or disorder or diagnostic treatment. In an aspect, the patient or the subject is a human patient or human subject. In an aspect the patient or subject is a domesticated companion animal such as a dog or cat.

The term "targeting moiety", as used herein, refers to a moiety that binds to or localizes to a specific target or locale. The moiety may be, for example, a protein, a nucleic acid, a nucleic acid analog, a carbohydrate, an antibody, or a small molecule. The locale may be a tissue, a particular cell type, or a subcellular compartment. The targeting moiety or a sufficient plurality of targeting moieties may be used to direct the localization of a particle or an active entity.

Chemical Definitions

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

The term "isonitrile" as used herein refers to the group —NC or —N≡C. In a compound including an isonitrile, the isonitrile is linked to the compound via the nitrogen atom. The resonance structures of the isonitrile group are illustrated below:

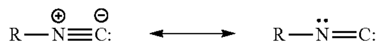

The term "isonitrile" is synonymous with "isocyanide" as it appears in some pertinent literature.

The term "alkylene" as used herein refers to a divalent alkyl group and may be linear or branched.

The term "aldehyde" as used herein refers to —C(═O)H.

The term "alkylene aldehyde" as used herein refers to an alkylene group attached to an aldehyde group.

The term "ketone" as used herein refers to the formula —C(═O)-alkyl. The alkyl group may be linear or branched.

The term "alkylene ketone" as used herein refers to the formula -alkylene-C(═O)-alkyl. The alkyl group may be linear or branched.

The term "ester" as used herein refers to the formula —C(═O)—O-alkyl or —O—C(═O)-alkyl. The alkyl group may be linear or branched.

The term "alkylene ester" as used herein refers to the formula -alkylene-C(═O)—O-alkyl or -alkylene-O—C(═O)-alkyl. The alkyl group may be linear or branched.

The term "amide" as used herein refers to the formula —C(═O)N(R)$_2$ or —N(R)—C(═O)-alkyl The R groups may each independently be hydrogen or linear or branched alkyl groups.

The term "alkylene amide" as used herein refers to the formula -alkylene-C(═O)NR$_1$R$_2$ or -alkylene-N(R$_1$)—C(═O)-alkyl The R groups may each independently be hydrogen or linear or branched alkyl groups. The alkylene and alkyl groups may be linear or branched.

The term "sulfonamide" as used herein refers to the formula —S(═O)N(R)$_2$ or —N(R)—S(═O)-alkyl Each occurrence of the R group may each independently be hydrogen or linear or branched alkyl groups.

The term "alkylene sulfonamide" as used herein refers to the formula -alkylene-S(═O)$_2$N(R)$_2$ or -alkylene-N(R)—S(═O)$_2$-alkyl Each occurrence of R may independently be hydrogen or a linear or branched alkyl group.

The term "carboxylic acid" as used herein refers to the formula —C(═O)OH.

The term "alkyl carboxylic acid" as used herein refers to the formula -alkylene-C(═O)OH.

The term "acyl hydrazide" as used herein refers to the formula —C(═O)NH—NH$_2$. The term "alkylene acyl hydrazide" as used herein refers to the formula -alkylene-C(═O)NH—NH$_2$.

The term "sulfonyl hydrazide" as used herein refers to the formula —S(═O)$_2$NH—NH$_2$. The term "alkylene acyl hydrazide" as used herein refers to the formula -alkylene-S(═O)$_2$NH—NH$_2$.

The term "phosphoryl hydrazide" as used herein refers to the formula —P(═O)NH—NH2. The term "alkylene phosphoryl hydrazide" as used herein refers to the formula -alkylene —P(═O)NH—NH$_2$.

The term "hydrazone" as used herein refers to the formula —C(═N—NH$_2$)-alkyl.

The term "alkylene hydrazone" as used herein refers to the formula -alkylene-C(═N—NH$_2$)-alkyl.

The term "sulfonate" as used herein refers to the formula —S(O)$_2$OR.

The term "alkylene sulfonate" as used herein refers to the formula -alkylene-S(O)$_2$OR.

The term "sulfonic acid" as used herein refers to the formula —S(O)$_2$OH.

The term "alkylene sulfonic acid" as used herein refers to the formula -alkylene-S(O)$_2$OH.

The term "amine" as used herein refers to the formula —N(R)$_3$. Each occurrence of R is independently hydrogen or alkyl. The amine can be a primary amine, a secondary amine, or a tertiary amine.

The term "alkylene amine" as used herein refers to the formula -alkylene-N(R)$_2$.

The term "urea" as used herein refers to the formula —N(R)C(═O)—N(R)$_2$ wherein each occurrence of R is independently a hydrogen or a linear or branched alkyl group.

The term "sulfonylurea" as used herein refers to the formula —N(R)S(═O)—N(R)$_2$ wherein each occurrence of R is independently a hydrogen or a linear or branched alkyl group.

The term "carbamate" as used herein refers to the formula —O—C(═O)—N(R)$_2$ or —N(R)—C(═O)—O(R) wherein each occurrence of R is independently a hydrogen or a linear or branched alkyl group.

The term "$C_1$-$C_{12}$ alkyl" as used herein refers to a linear or branched saturated aliphatic hydrocarbon having 1 to 12 carbon atoms, and non-limiting examples thereof include a methyl group, an ethyl group, a propyl group, an iso-butyl group, a sec-butyl group, a tert-butyl group, a pentyl group, an iso-amyl group, and a hexyl group.

The term "$C_1$-$C_{12}$ alkoxy" as used herein refers to a monovalent group represented by —OA$_{101}$ (wherein A$_{101}$ is the $C_1$-$C_{12}$ alkyl), and non-limiting examples thereof include a methoxy group, an ethoxy group, and an iso-propoxy group.

The term "$C_1$-$C_{12}$ alkylthio" as used herein refers to —SA$_{102}$ (wherein A$_{102}$ is the $C_1$-$C_{12}$ alkyl), and non-limiting examples thereof include a methylthio group, an ethylthio group, and an iso-propylthio group.

The term "$C_6$-$C_{12}$ aryloxy" as used herein refers to a monovalent group represented by —OA$_{103}$ (wherein A$_{131}$ is the $C_6$-$C_{12}$ aryl group), and non-limiting examples thereof include a phenoxy group and a naphthoxy group.

The term "$C_6$-$C_{12}$ arylthio" as used herein refers to a monovalent group represented by —SA$_{104}$ (wherein A$_{104}$ is the $C_6$-$C_{12}$ aryl group), and non-limiting examples thereof include a phenylthiol group and a naphthylthio group.

The term "$C_2$-$C_{12}$ alkenyl" as used herein refers to a hydrocarbon group formed by including at least one carbon-carbon double bond in the middle or at the terminus of the $C_2$-$C_{12}$ alkyl group, and examples thereof include an ethenyl group, a propenyl group, and a butenyl group. The term "$C_2$-$C_{12}$ alkenylene group" as used herein refers to a divalent group having the same structure as the $C_2$-$C_{12}$ alkenyl group.

The term "$C_2$-$C_{12}$ alkynyl group" as used herein refers to a hydrocarbon group formed by including at least one carbon-carbon triple bond in the middle or at the terminus of the $C_2$-$C_{12}$ alkyl group, and examples thereof include an ethynyl group, and a propynyl group. The term "$C_2$-$C_{12}$ alkynylene group" as used herein refers to a divalent group having the same structure as the $C_2$-$C_{60}$ alkynyl group.

The term "$C_3$-$C_7$ cycloalkyl group" as used herein refers to a monovalent saturated hydrocarbon monocyclic group having 3 to 7 carbon atoms, and non-limiting examples thereof include a cyclopropyl group, a cyclobutyl group, a cyclopentyl group, a cyclohexyl group, and a cycloheptyl group. The term "$C_3$-$C_7$ cycloalkylene group" as used herein refers to a divalent group having the same structure as the $C_3$-$C_7$ cycloalkyl group.

The term "a ($C_1$-$C_6$ alkyl)$C_3$-$C_7$ cycloalkyl group" as used herein refers to a monovalent saturated hydrocarbon monocyclic group having 3 to 7 carbon atoms attached to an alkylene group. A non-limiting example includes a —CH$_2$-cyclopropyl group.

The term "$C_2$-$C_7$ heterocycloalkyl group" as used herein refers to a monovalent saturated monocyclic group having at least one heteroatom and 2 to 7 carbon atoms, and non-limiting examples thereof include a tetrahydrofuranyl group, and a tetrahydrothiophenyl group. The term "$C_2$-$C_7$ heterocycloalkylene group" as used herein refers to a divalent group having the same structure as the $C_2$-$C_7$ heterocycloalkyl group.

The term "($C_1$-$C_6$ alkyl)$C_2$-$C_7$ heterocycloalkyl group" as used herein refers to a monovalent saturated monocyclic group having at least one heteroatom and 2 to 7 carbon atoms attached to an alkylene group. A non-limiting example includes a —CH2-tetrahydrofuranyl group.

The term "$C_3$-$C_7$ cycloalkenyl group" as used herein refers to a monovalent monocyclic group that has 3 to 7 carbon atoms and at least one carbon-carbon double bond in the ring thereof and that has no aromaticity, and non-limiting examples thereof include a cyclopentenyl group, a cyclohexenyl group, and a cycloheptenyl group. The term "$C_3$-$C_7$ cycloalkenylene group" as used herein refers to a divalent group having the same structure as the $C_3$-$C_{10}$ cycloalkenyl group.

The term "$C_2$-$C_7$ heterocycloalkenyl group" as used herein refers to a monovalent monocyclic group that has at least one heteroatom as a ring-forming atom, 2 to 7 carbon atoms, and at least one carbon-carbon double bond in its ring. Examples of the $C_2$-$C_7$ heterocycloalkenyl group are a 2,3-dihydrofuranyl group, and a 2,3-dihydrothiophenyl group. The term "$C_2$-$C_7$ heterocycloalkenylene group" as used herein refers to a divalent group having the same structure as the $C_2$-$C_7$ heterocycloalkenyl group.

The term "($C_1$-$C_6$ alkyl) $C_2$-$C_7$ heterocycloalkenyl group" refers to a monovalent heterocycloalkenyl group, attached to an alkylene group.

The term "$C_6$-$C_{12}$ aryl" as used herein refers to a monovalent group having a carbocyclic aromatic system having 6 to 12 carbon atoms, and the term "$C_6$-$C_{12}$ arylene" as used herein refers to a divalent group having a carbocyclic aromatic system having 6 to 12 carbon atoms. Non-limiting examples of the $C_6$-$C_{12}$ aryl group include a phenyl group and a naphthyl group. When the $C_6$-$C_{12}$ aryl group and the $C_6$-$C_{12}$ arylene group each include two or more rings, the rings may be fused to each other.

The term "($C_1$-$C_6$ alkyl)$C_6$-$C_{12}$ aryl" refers to a monovalent aryl group, attached to an alkylene group. Non-limiting examples of a ($C_1$-$C_6$ alkyl)$C_6$-$C_{12}$ aryl include a —$CH_2$-phenyl group and a —$CH_2$-biphenyl group.

The term "$C_2$-$C_{12}$ heteroaryl" as used herein refers to a monovalent group having a carbocyclic aromatic system that has at least one heteroatom as a ring-forming atom, and 2 to 12 carbon atoms. The term "$C_2$-$C_{12}$ heteroarylene" as used herein refers to a divalent group having a carbocyclic aromatic system that has at least one heteroatom as a ring-forming atom, and 2 to 12 carbon atoms. Non-limiting examples of the $C_2$-$C_{12}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{12}$ heteroaryl group and the $C_2$-$C_{12}$ heteroarylene group each include two or more rings, the rings may be fused to each other.

The term "($C_1$-$C_6$ alkyl)$C_3$-$C_{12}$ heteroaryl" refer to a monovalent heteroaryl group, attached to an alkylene group. A non-limiting example of a ($C_1$-$C_6$ alkyl)$C_3$-$C_{12}$ heteroaryl group is a —$CH_2$-pyridyl group.

The term "$C_6$-$C_{12}$ aryloxy group" as used herein indicates —$OA_{102}$ (wherein $A_{102}$ is the $C_6$-$C_{12}$ aryl group), and the term a "$C_6$-$C_{12}$ arylthio group" as used herein indicates —$SA_{103}$ (wherein $A_{103}$ is the $C_6$-$C_{12}$ aryl group).

The terms "$C_3$-$C_6$ carbocyclic" and "$C_5$-$C_7$ carbocyclic" as used herein refers to a saturated or unsaturated cyclic group having, 3 to 6 carbons or 5 to 7 carbons, respectively, as ring-forming atoms.

The term "$C_2$-$C_6$ heterocyclic" as used herein refers to a saturated or unsaturated cyclic group having at least one heteroatom and 2 to 6 carbon atoms as ring-forming atoms.

The term "spiro ring system" refers to a ring system having at least two rings that share only one common ring-forming atom.

Unless substituents are otherwise specifically indicated, each of the foregoing groups can be unsubstituted or substituted, provided that the substitution does not significantly adversely affect synthesis, stability, or use of the compound. "Substituted" means that the compound, group, or atom is substituted with at least one (e.g., 1, 2, 3, or 4) substituents instead of hydrogen, where each substituent is independently nitro (—$NO_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g., benzyl), $C_{7-12}$ alkylarylene (e.g, toluyl), $C_{4-12}$ heterocycloalkyl, $C_{3-12}$ heteroaryl, $C_{1-6}$ alkyl sulfonyl (—S(=O)$_2$-alkyl), $C_{6-12}$ arylsulfonyl (—S(=O)$_2$-aryl), or tosyl ($CH_3C_6H_4SO_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the compound or group, including those of any substituents.

Compounds

Disclosed herein are compounds and pharmaceutically acceptable salts thereof which can bind and inhibit the activity of one or more CYPs. The compound or pharmaceutically acceptable salt thereof includes at least one isonitrile group (—NC). In an aspect, the compound is represented by Formula 1:

(Formula 1)

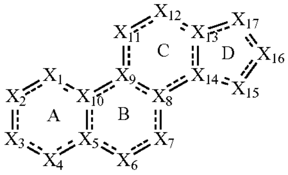

wherein $X_1$ is N, N($R_{11}$), C($R_{11}$), O, S, S(=O), C(=Y), C(=N—$OR_{11}$), C($R_{11}$)($R_{12}$), or L(N≡C);

$X_2$ is N, N($R_{21}$), C($R_{21}$), O, S, S(=O), C(=Y), C(=N—$OR_{21}$), C($R_{21}$)($R_{22}$), or L(N≡C);

$X_3$ is N, N($R_{31}$), C($R_{31}$), O, S, S(=O), C(=Y), C(=N—$OR_{31}$), C($R_{31}$)($R_{32}$), or L(N≡C);

$X_4$ is N, N($R_{41}$), C($R_{41}$), O, S, S(=O), C(=Y), C(=N—$OR_{41}$), C($R_{41}$)($R_{42}$), or L(N≡C);

$X_5$ is C, N, C($R_{51}$), or L(N≡C);

$X_6$ is N, N($R_{61}$), C($R_{61}$), O, S, S(=O), C(=Y), C(=N—$OR_{61}$), C($R_{61}$)($R_{62}$), or L(N≡C);

$X_7$ is N, N($R_{71}$), C($R_{71}$), O, S, S(=O), C(=Y), C(=N—$OR_{71}$), C($R_{71}$)($R_{72}$), or L(N≡C);

$X_8$ is C, N, C($R_{81}$), or L(N≡C);

$X_9$ is C, N, C($R_{91}$), or L(N≡C);

$X_{10}$ is C, N, C($R_{101}$), or L(N≡C);

$X_{11}$ is N, N($R_{111}$), C($R_{111}$), O, S, S(=O), C(=Y), C(=N—$OR_{111}$), C($R_{111}$)($R_{112}$), or L(N≡C);

$X_{12}$ is N, N($R_{121}$), C($R_{121}$), O, S, S(=O), C(=Y), C(=N—$OR_{121}$), C($R_{121}$)($R_{122}$), or L(N≡C);

$X_{13}$ is C, N, C($R_{131}$), or L(N≡C);

$X_{14}$ is C, N, C($R_{141}$), or L(N≡C);

$X_{15}$ is N, N($R_{151}$), C($R_{151}$), O, S, S(=O), C(=Y), C(=N—$OR_{151}$), C($R_{151}$)($R_{152}$) or L(N≡C);

$X_{16}$ is N, N($R_{161}$), C($R_{161}$), O, S, S(=O), C(=Y), C(=N—$OR_{161}$), C($R_{161}$)($R_{162}$) or L(N≡C);

$X_{17}$ is N, N($R_{171}$), C($R_{171}$), O, S, S(=O), C(=Y), C(=N—$OR_{171}$), C($R_{171}$)($R_{172}$) or L(N≡C);

Y is N, O, S, or $C_1$-$C_{12}$ alkyl in which any carbon-carbon single bond is optionally replaced by a carbon-carbon double or triple bond, any methylene is optionally replaced by O, S, or $NR^{10}$, and optionally substituted with one or more substituents independently chosen from halogen, hydroxyl, cyano, amino, thio (═S), and oxo (═O);

$R_{10}$, $R_{11}$, $R_{12}$, $R_{21}$, $R_{22}$, $R_{31}$, $R_{32}$, $R_{41}$, $R_{42}$, $R_{51}$, $R_{61}$, $R_{62}$, $R_{71}$, $R_{81}$, $R_{91}$, $R_{101}$, $R_{111}$, $R_{112}$, $R_{121}$, $R_{122}$, $R_{131}$, $R_{141}$, $R_{151}$, $R_{152}$, $R_{161}$, $R_{162}$, $R_{171}$, and $R_{172}$ are each independently hydrogen, deuterium, hydroxyl, halogen, $C_1$-$C_{12}$ alkyl in which any carbon-carbon single bond is optionally replaced by a carbon-carbon double or triple bond, any methylene is optionally replaced by O, S, Si, Ge, P, or $NR^{10}$, and optionally substituted with one or more substituents independently chosen from halogen, hydroxyl, cyano, amino, and oxo;

L is a single bond or a $C_1$-$C_{12}$ alkyl in which any carbon-carbon single bond is optionally replaced by a carbon-carbon double or triple bond, any methylene is optionally replaced by O, S, Si, Ge, P, or $NR^{10}$, and optionally substituted with one or more substituents independently chosen from halogen, hydroxyl, cyano, amino, and oxo;

optionally, any two adjacent substituents may form a $C_5$-$C_7$ carbocyclic ring or a $C_2$-$C_7$ heterocyclic ring;

optionally, any two substituents on the same carbon may form a carbocyclic or heterocyclic spiro ring system with any of rings A-D; and ------ represents a single or a double bond provided that rings A, B, C, and D are not simultaneously aromatic.

In an aspect, in Formula 1, $R_{10}$, $R_{11}$, $R_{12}$, $R_{21}$, $R_{22}$, $R_{31}$, $R_{32}$, $R_{41}$, $R_{42}$, $R_{51}$, $R_{61}$, $R_{62}$, $R_{71}$, $R_{81}$, $R_{91}$, $R_{101}$, $R_{111}$, $R_{112}$, $R_{121}$, $R_{122}$, $R_{131}$, $R_{141}$, $R_{151}$, $R_{152}$, $R_{161}$, $R_{162}$, $R_{171}$, and $R_{172}$ are each independently:

hydrogen, deuterium, halogen, aldehyde, alkylene aldehyde, ketone, alkylene ketone, ester, alkylene ester, amide, alkylene amide, sulfonamide, alkylene sulfonamide, carbamate, alkylene carbamate, urea, alkylene urea, sulfonyl urea, alkylene sulfonyl urea, carboxylic acid, alkylene carboxylic acid, cyano, hydroxyl, thiol, nitro, acyl hydrazide, sulfonyl hydrazide, phosphoryl hydrazide, acyl hydrazone, sulfonic acid, alkylene sulfonic acid, sulfonate, alkylene sulfonate, amine, alkylene amine, $C_1$-$C_{12}$ alkyl, $C_2$-$C_{12}$ alkenyl, $C_2$-$C_{12}$ alkynyl, $C_1$-$C_{12}$ alkoxy, $C_1$-$C_{12}$ alkylthio, $C_3$-$C_7$ cycloalkyl, $C_1$-$C_6$ alkyl($C_3$-$C_7$ cycloalkyl), $C_1$-$C_6$ alkyl ($C_3$-$C_7$ cycloalkenyl), $C_3$-$C_7$ cycloalkenyl, $C_2$-$C_7$ heterocycloalkyl, $C_2$-$C_7$ heterocycloalkenyl, $C_1$-$C_6$ alkyl ($C_2$-$C_7$ heterocycloalkyl), $C_1$-$C_6$ alkyl($C_2$-$C_7$ heterocycloalkenyl), $C_6$-$C_{12}$ aryl, $C_2$-$C_{12}$ heteroaryl, $C_1$-$C_6$ alkyl ($C_2$-$C_{12}$ heteroaryl), optionally substituted with hydroxyl, halogen, deuterium, $Si(Q_3)(Q_4)(Q_5)$, $—Ge(Q_3)(Q_4)(Q_5)$, $—B(Q_6)(Q_7)$, $—P(═O)(Q_8)(Q_9)$, $—P(Q_8)(Q_9)$, wherein $Q_1$ to $Q_9$ are each independently: hydrogen; deuterium; halogen, hydroxyl; cyano; $C_1$-$C_6$ alkyl; $C_2$-$C_6$ alkenyl; $C_2$-$C_6$ alkynyl; $C_1$-$C_6$ alkoxy; $C_3$-$C_6$ carbocyclic; or $C_2$-$C_6$ heterocyclic. In any of the foregoing, it is contemplated that one or more carbon-carbon single bonds of the alkyl and alkylene groups may be replaced with a double bond or triple bond.

In some aspects, in Formula 1, heteroaryl groups are excluded from $R_{10}$, $R_{11}$, $R_{12}$, $R_{21}$, $R_{22}$, $R_{31}$, $R_{32}$, $R_{41}$, $R_{42}$, $R_{51}$, $R_{61}$, $R_{62}$, $R_{71}$, $R_{81}$, $R_{91}$, $R_{101}$, $R_{111}$, $R_{112}$, $R_{121}$, $R_{122}$, $R_{131}$, $R_{141}$, $R_{151}$, $R_{152}$, $R_{161}$, $R_{162}$, $R_{171}$, and $R_{172}$. In certain aspects, azole groups (e.g., tetrazole) are excluded from $R_{10}$, $R_{11}$, $R_{12}$, $R_{21}$, $R_{22}$, $R_{31}$, $R_{32}$, $R_{41}$, $R_{42}$, $R_{51}$, $R_{61}$, $R_{62}$, $R_{71}$, $R_{81}$, $R_{91}$, $R_{101}$, $R_{111}$, $R_{112}$, $R_{121}$, $R_{122}$, $R_{131}$, $R_{141}$, $R_{151}$, $R_{152}$, $R_{161}$, $R_{162}$, $R_{171}$, and $R_{172}$.

In an aspect, the compound of Formula 1 is represented by Formula 1-A to Formula 1-E and $X_1$ to $X_{17}$ are the same as defined for Formula 1.

Formula 1-A

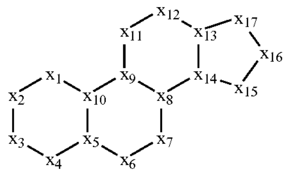

Formula 1-B

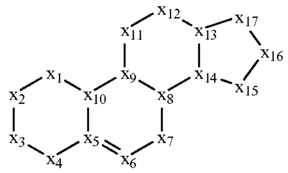

Formula 1-C

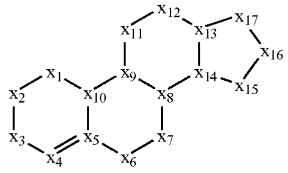

Formula 1-D

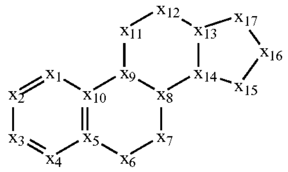

Formula 1-E

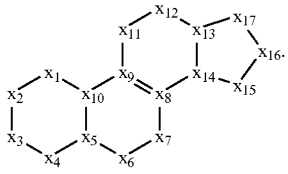

In an aspect, the compound is of the following formulae and $X_1$ to $X_{17}$ are the same as defined for Formula 1. Z is the same as defined for $X_1$ in Formula 1.

Formula 1-A-1

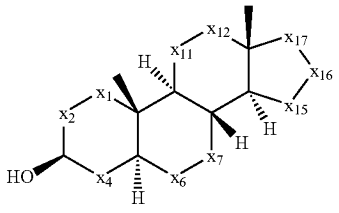

-continued

Formula I-B-1

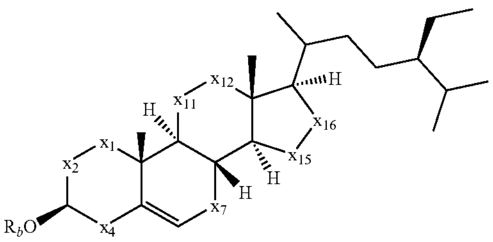

Formula I-B-2

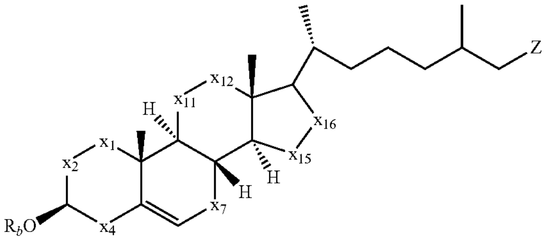

Formula I-C-1

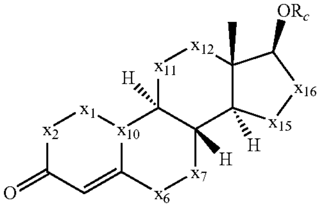

Formula I-D-1

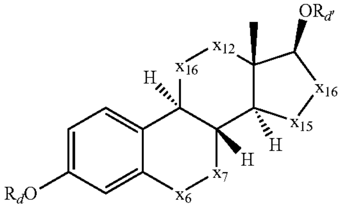

Formula 1-E-1

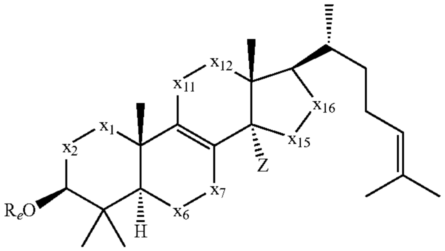

In Formulae 1A-1, 1-B-1, 1-B-2, 1-C-1, 1-D-1, and 1-E-1, $R_a$ to $R_e$ are each independently hydrogen or a protecting group. Protecting groups may include any hydroxyl protecting group known in the art. Non-limiting exemplary protecting groups include: acetyl, benzoyl, benzyl, methoxymethyl ether, methoxyethoxymethyl ether, dimethoxytrityl, p-methoxybenzyl ether, p-methoxyphenyl ether, methylthiomethyl ether, pivaloyl ester, tetrahydropyranyl ether, tetrahydrofuran ether, trityl, silyl ether, and the like.

In Formulae 1A-1, 1-B-1, 1-B-2, 1-C-1, 1-D-1, and 1-E-1, the members of rings A, B, C, and D may all be carbon.

Representative structures of the compound of Formula 1 or a pharmaceutically acceptable salt thereof include the following compounds.

3a

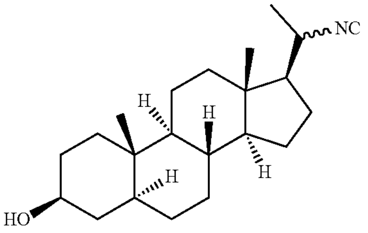

3b

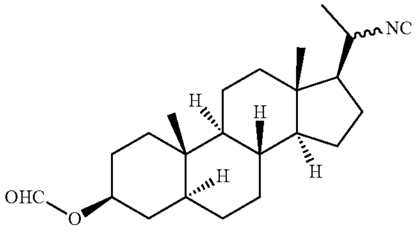

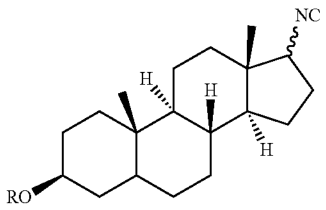

6a: R = H;
6b: R = CHO;
6c: R = acetyl

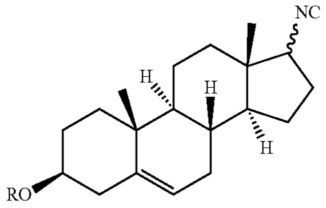

6d: R = H;
6e: R = CHO;
6f: R = acetyl

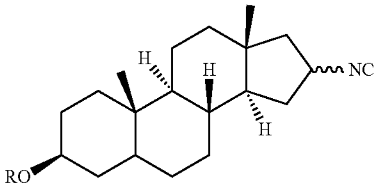

6a-16: R = H;
6b-16: R = CHO;
6c-16: R = acetyl

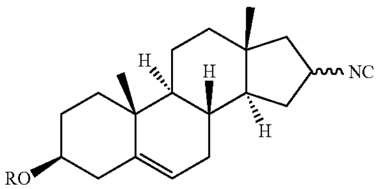

6d-16: R = H;
6e-16: R = CHO;
6f-16: R = acetyl

-continued
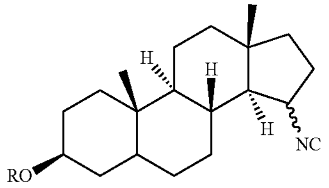
6a-15: R = H;
6b-15: R = CHO;
6c-15: R = acetyl
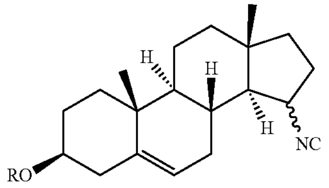
6d-15: R = H;
6e-15: R = CHO;
6f-15: R = acetyl
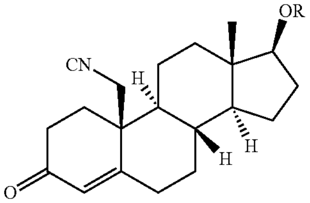
10a: R = OH;
10b: R = CHO;
10c: R = acetyl
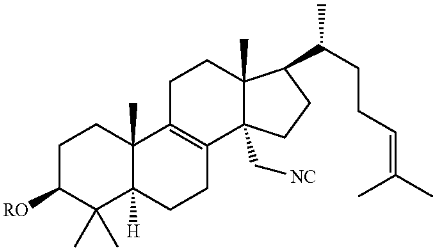
11a: R = OH;
11b: R = CHO;
11c: R = acetyl
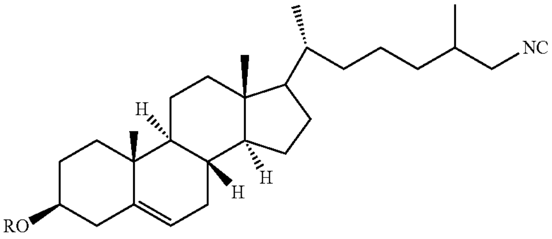
12a: R = OH;
12b: R = CHO;
12c: R = acetyl
13a
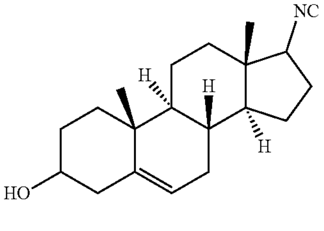
-continued
13b
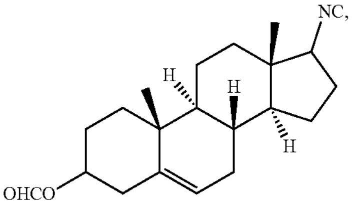
14a
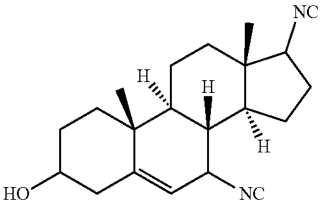
14b
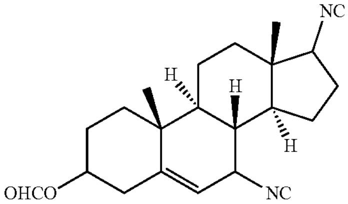
15a
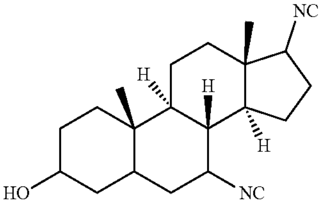
15b
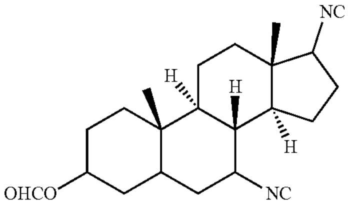
16
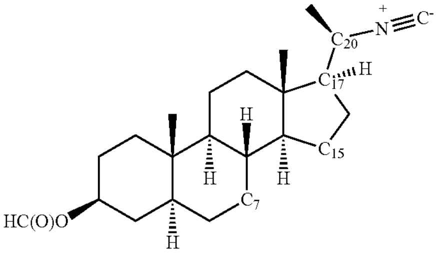
17
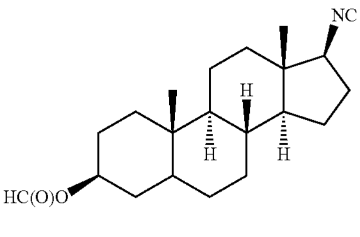

-continued

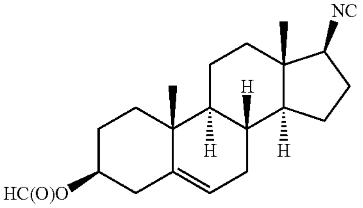

18

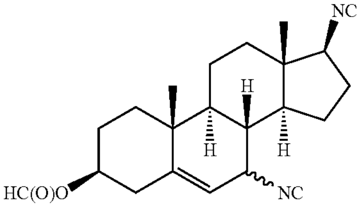

19

The compounds disclosed herein may be synthesized using any method known to those of ordinary skill in the art via total synthetic methods or using enzymatic transformation.

A method for providing a chemical structure of an isonitrile inhibitor of a cytochrome P450 comprises (a) oxidizing a parent compound with a cytochrome P450 to provide an oxidation product comprising an oxidized functional group; (b) determining a chemical structure of the oxidation product; and (c) replacing the oxidized functional group with a carbon-isonitrile functional group to provide a structure of an isonitrile inhibitor of the cytochrome P450. In an aspect, the parent compound comprises a steroid and/or a steroid-derivative. In an aspect, the parent compound comprises a steroid and/or a steroid-derivative having a ketone functional group. In an exemplary embodiment, the parent compound androsterone was oxidized by CYP106A2, which results in multiple oxidation products. After isolation of the oxidation products using purification methods known in the art (e.g., recrystallization, HPLC purification), the oxidation products were characterized using NMR methods to determine the chemical structure of each oxidation product. The chemical structure of each isonitrile inhibitor was obtained by substituting the oxidized carbon(s) of each oxidation product with an isonitrile group. The ability of each isonitrile inhibitor to bind CYP106A2 was assessed to determine those inhibitors with the strongest inhibition of CYP106A2. The results of the assay are shown in FIG. 3C for an isonitrile inhibitor (see compound 19) obtained from androsterone substituted with two isonitrile groups (i.e., at the 7 and 17 positions).

A pharmaceutically acceptable salt includes salts that retain the biological effectiveness and properties of the compound, and which are not biologically or otherwise undesirable, and include derivatives of the disclosed compounds in which the parent compound is modified by making inorganic and organic, non-toxic, acid or base addition salts thereof. The salts can be synthesized from the parent compound by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable.

Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wermuth, Editors, Wiley-VCH, 2002.

A salt of the compounds disclosed herein further includes solvates of the compounds and of the compound salts. A "solvate" means the compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. In an aspect, the solvate is a hydrate.

The above described compounds or a pharmaceutically acceptable salt thereof are also referred to herein collectively as "isonitrile compounds", for ease of explanation.

The isonitrile compounds are derived from a steroid or steroid-like structure, and can be readily synthesized from a molecule having appropriately positioned carbonyl groups. See for example, Reaction Schemes 1 and 2 in the Examples.

The disclosed isonitrile compounds lend themselves to the generation of compound libraries, which when combined with commercially available CYP screening libraries, makes the spectroscopic identification of complexes straightforward. Furthermore, the spectroscopic measurement of dissociation constants ($K_d$) can be used assess the relative binding between the compound and the CYP in a given CYP-inhibitor complex. The better the fit of the CYP inhibitor into the enzyme active site, the tighter the binding and the lower $K_d$.

Pharmaceutical Description

The disclosed compounds of Formula (1) or pharmaceutically acceptable salts thereof (isonitrile compounds) are designed to inhibit the activity of at least one CYP enzyme, and are thus CYP inhibitors. The present disclosure provides compositions comprising the disclosed isonitrile compounds as well as methods of treating a subject with the isonitrile compounds. The isonitrile compounds can be administered to a subject to inhibit the activity of one or more CYP enzyme in a subject. The CYP activity can be associated with the progression of a disease or can be associated with the decreased efficacy of a drug designed to treat or prevent the disease.

The present disclosure provides a method of inhibiting activity of a cytochrome P450 (CYP) in a subject having a steroid-responsive cancer, an antibiotic-resistant *Mycobacterium tuberculosis* infection, a fungal infection, or a trypanosome infection, the method comprising administering to the subject an isonitrile compound disclosed herein, or a pharmaceutically acceptable salt thereof, in an amount effective to inhibit the CYP activity in the subject.

In an aspect, the subject has a steroid-responsive cancer. In an aspect, a method of treating a steroid-responsive cancer in a subject comprises administering to the subject an isonitrile compound disclosed herein in an amount effective to treat the steroid-responsive cancer in the subject. The steroid-responsive cancer includes, for example, prostate cancer, acute lymphoblastic leukemia, acute myeloid leukemia, chronic lymphocytic leukemia, chronic myeloid leukemia, Hodgkin's lymphoma, non-Hodgkin's lymphoma, multiple myeloma, breast cancer, ovarian cancer, or a combination thereof. In an aspect, the steroid responsive cancer is prostate cancer and the CYP is CYP17A1.

In an aspect, the subject has a *Mycobacterium tuberculosis* (Mtb) infection. Mtb is unable to synthesize steroids, but requires cholesterol for survival. In order to survive, the Mtb organism must take up and metabolize cholesterol from the infected human host. Three CYPs (CYP124A1, CYP125A1 and CYP142A1) have been identified as being involved in primary metabolism of steroids by Mtb (Johnston et al., Bioorg. Med. Chem. 20 (2012), 4064-4081). The steroids metabolized by CYP124A1, CYP125A1 and/or CYP142A1 and utilized by Mtb include cholesterol, 27-norcholesterol, 25-thia-27-norcholesterol, cholesta-5,25-dienol, 26-methylcholesta-5,25(26)-dienol, 26-methylcholesterol, 27-norcholesta-5,25-dienol, 25-chloro-27-norcholesterol, 25-bromo-27-borcholesterol, 24-bromochol-5-enol, desmosterol, coprosterol, lanosterol, and cholest-4-en-3-one. which shows the various types of steroids that are metabolized by these enzymes (Johnston et al., supra). Each of the CYP enzymes appear to act on the terminal (ω-) carbon of the sterol side chain regardless of the precise nature of the steroid. Cholesterol is shown below as an example.

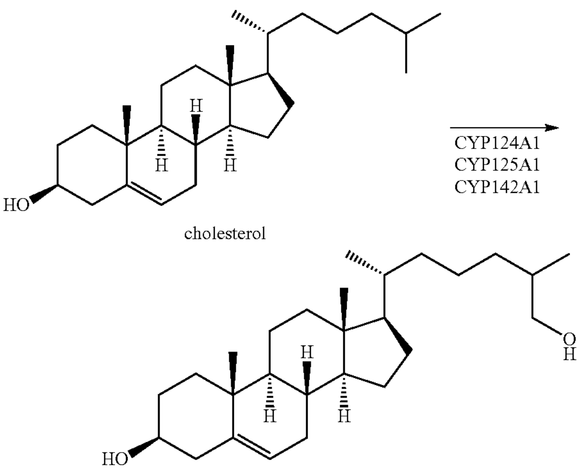

cholesterol

In an aspect, a method of treating a *Mycobacterium tuberculosis* infection in a subject includes administering to the subject an isonitrile compound disclosed herein in an amount effective to treat the *Mycobacterium tuberculosis* infection in the subject. In an aspect, the Mtb is an antibiotic resistant strain. In an aspect, the isonitrile compound inhibits activity of a cytochrome P450 (CYP) in the subject. In an aspect, the CYP comprises CYP124A1, CYP125A1, CYP142A1, or a combination thereof.

In an aspect, the subject has a fungal infection. The fungal infection can be caused by a fungus such as, for example, *Aspergillus* sp, *Blastomyces* sp, *Candida* sp, *Coccidiodes* sp, *Crytococcus* sp, *Epidermophyton* sp, *Histoplasma* sp, *Malassezia* sp, *Microsporum* sp, *Mucor* sp, *Paracoccidioides* sp, *Pityriasis* sp, *Pneumocystis* sp, *Rhizopus* sp, *Trichophytan* sp, or a combination thereof. In an aspect, the subject has a disease caused by the fungal infection.

In an aspect, a method of treating a fungal infection in a subject comprises administering to the subject an isonitrile compound disclosed herein in an amount effective to treat or prevent the fungal infection in the subject. In an aspect, the isonitrile compound inhibits activity of a cytochrome P450 (CYP) in the subject. In an aspect, the CYP comprises CYP51.

In an aspect, the subject has a trypanosome (parasite) infection. The trypanosome infection can be caused by, for example *Trypanosome cruzi, Trypanosome brucei gambiense*, or *Trypanosome brucei rhodesiense*. In an aspect, the subject has a disease caused by a trypanosome infection, for example, sleeping sickness or Chagas' disease. In an aspect, a method of treating a trypanosome infection in a subject comprising administering to the subject an isonitrile compound disclosed herein in an amount effective to treat or prevent the trypanosome infection in the subject. In an aspect, the isonitrile compound inhibits activity of a cytochrome P450 (CYP) in the subject. In an aspect, the CYP comprises CYP51.

The isonitrile compounds disclosed herein can be administered in the form of a composition including one or more isonitrile compound. In an aspect, the composition is a pharmaceutical composition including the isonitrile compound and a pharmaceutically acceptable carrier.

The isonitrile groups in the disclosed isonitrile compounds are acid labile. The acid lability of the isonitrile group can be protected by encapsulating the isonitrile compound within a protective shell. In an aspect, a composition includes a plurality of encapsulated nanoparticles, wherein each of the encapsulated nanoparticles independently comprises a core comprising an isonitrile compound disclosed herein or a pharmaceutically acceptable salt thereof, and an outer shell at least partially encapsulating the core. A "nanoparticle" is a particle having an average diameter of less than one micrometer.

The plurality of nanoparticles can have a liquid-filled core or a particulate core. The core is at least partially encapsulated by an outer shell. In an aspect, the nanoparticles are completely encapsulated (surrounded) by the outer shell. The outer shell of the plurality of nanoparticles can be a lipid monolayer, a lipid bilayer, a polymer layer, or a combination thereof, and can be unilamellar or multilamellar. In an aspect, the plurality of encapsulated nanoparticles are nanodroplets having a liquid-filled core and a stabilizing outer shell. A "nanodroplet" as used herein refers to droplets that are less than one micrometer in size that are partially or completely encapsulated or encased or surrounded by the outer shell.

The lipid layer is composed of one or more biocompatible lipids. Non-limiting examples of lipids include sterols, cholesterol, phospholipids, lysolipids, lysophospholipids, sphingolipids, ceramides, pegylated lipids, and combinations thereof.

The polymer layer is composed of at least one biocompatible and biodegradable polymer. The biodegradable polymers can form a biodegradable polymer matrix. Biodegradable polymers can include polymers that are insoluble or sparingly soluble in water that are converted chemically or enzymatically in the body into water-soluble materials. Non-limiting examples of biodegradable polymers include polyamides, polycarbonates, polyalkylenes, polyalkylene glycols, polyalkyl glycols polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexylmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. In an aspect, the biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, poly(alkylamines), derivatives thereof, linear and branched copolymers and block copolymers thereof, or a combination thereof.

In an aspect, the nanoparticles are lipid nanoparticles including a lipid-containing shell. The lipid nanoparticles include lipid micelles, liposomes, solid lipid nanoparticles, or a combination thereof. Lipid micelles and methods of their preparation are known in the art. For example, lipid micelles can be formed as a water-in-oil emulsion with a lipid surfactant to stabilize the dispersed droplets. In some embodiments, the lipid micelle is a microemulsion. A microemulsion is a thermodynamically stable system composed of at least water, oil and a lipid surfactant, having a droplet size of less than 1 micron, from about 10 nm to about 500 nm, or from about 10 nm to about 250 nm. Liposomes are small vesicles composed of an aqueous medium surrounded by lipids arranged in spherical bilayers. Liposomes can be small unilamellar vesicles, large unilamellar vesicles, or small or large multi-lamellar vesicles. Multi-lamellar liposomes contain multiple concentric lipid bilayers. Liposomes can be used to encapsulate agents, by trapping hydrophilic agents in the aqueous interior or between bilayers, or by trapping hydrophobic agents within the bilayer. Solid lipid nanoparticles are formed of lipids that are solids at room temperature, and are derived from oil-in-water emulsions by replacing the liquid oil by a solid lipid.

In an aspect, the plurality of nanoparticles further includes a targeting moiety linked to the outer shell. The presence of the targeting moiety on the outer shell (outer surface) facilitates the delivery of the plurality of nanoparticles and their contents to a specific cell, subcellular compartment, tissue, organ, or organ system. The methods can include targeted delivery of the plurality of nanoparticles with little or no systemic delivery or systemic toxicity. The target region can be the specific cell, tissue, organ, or organ system. Non-limiting examples of the targeting moiety include a protein, a nucleic acid, a nucleic acid analog, a carbohydrate, an antibody, a small molecule, or a combination thereof.

The targeting moiety can be directly linked to the outer shell and/or the outer shell can include a linker for attaching the targeting moiety. The linker can be, for example, covalently attached on one end to the outer shell of the nanoparticle and opposite end of the linked can be covalently attached to the targeting moiety. The linker can be attached to the outer shell after the formation of the nanoparticles or during their formation.

In an aspect, the present disclosure provides a method of targeted delivery of an active agent to a target region in a subject in need thereof, the method comprising administering the compositions disclosed herein to the subject. In an aspect, the target region is a cell, tissue, organ, or organ system to which the targeting moiety binds. In an aspect, the subject has a steroid-resistant cancer and the target region is a tumor.

The disclosed isonitrile compounds or compositions including the isonitrile compounds can be administered to a subject using any known route of administration. For example, the administration can be systemic or localized to a specific site. Routes of administration include, but are not limited to, oral, topical, parenteral, intravenous, cutaneous, subcutaneous, intramuscular, inhalation or spray, sublingual, transdermal, intravenous, intrathecal, buccal, nasal, vaginal, rectal, or a combination thereof.

The isonitrile compounds or compositions including the isonitrile compounds are formulated for administration to the subject in a suitable dosage form. The dosage form can be, for example, a capsule, a tablet, an implant, a troche, a lozenge, a minitablet, a suspension, an emulsion, a solution, an aerosol, an inhalant, an injectable, an ovule, a gel, a wafer, a chewable tablet, a powder, a granule, a film, a sprinkle, a pellet, a topical formulation, a patch, a bead, a pill, a powder, a triturate, a smart pill, a smart capsule, a platelet, a strip, or a combination thereof.

In an aspect, the dosage form is an aerosol or inhalant formulated for nasal administration and pulmonary delivery. The aerosol can include a composition including the isonitrile compound as disclosed herein and a propellant. Non-limiting examples of propellants include HFA-134a (1,1,1,2-tetrafluoroethane), HFA-227 (1,1,1,2,3,3,3-heptafluoropropane), propellants such as those commonly referred to as Propellant 11 (trichlorofluoromethane), Propellant 12 (dichlorodifluoromethane), Propellant 114 (dichlorotetrafluoroethane), Propellant 113 (1,1,2-trichloro-1,2,2-trifluoroethane), Propellant 142b (1-chloro-1,1-difluoroethane), Propellant 152a (1,1-Difluoroethane), HCFC-123 (1,1,1-trifluoro-2,2-dichloroethane), HCFC-124 (1,1,1,2-tetrafluorochloroethane), HCFC-141b (1,1-dichloro-1-fluoroethane), HCFC-225 (2,2-Dichloro-1,1,1,3,3-pentafluoropropane), HFC-125 (pentafluorethane), FC-C51-12 (perfluorodimethylcyclobutane), 1,1-difluoroethane (DYMEL® 152a), dimethyl ether (DYMEL® A), pentane, or a combination thereof. Non-limiting examples of adjuvants include $C_2$-$C_6$ aliphatic alcohols and polyols such as ethanol, isopropanol, and propylene glycol. Non-limiting examples of the surfactant include L-a-phosphatidylcholine (PC), 1,2-dipalmitoylphosphatidyl-choline (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, sunflower seed oil, or a combination thereof.

An effective amount of the isonitrile compound can be provided in one or more of the above-described dosage forms. In an aspect, the dosage form is provided to the patient. In an aspect the effective amount of the isonitrile compound is administered to the patient as a single dose or a plurality of doses. For example, the subject can be administered 1 to 4 daily doses.

The isonitrile compounds can be administered alone or in combination with an additional active agent. Combination use includes an administering of the isonitrile compound and additional active agent in a single dosage form, or in separate dosage forms, either simultaneously or sequentially. The dose of the isonitrile compound when used in combination with a second active agent can be similar to the dose used for administration of the isonitrile compound alone. Doses and methods of administration of other therapeutic agents can be found, for example, in the manufacturer's instructions in the Physician's Desk Reference.

It will be understood, however, that the specific dose level for any particular patient receiving the isonitrile compound alone or in combination with an additional active agent, will depend upon a variety of factors including the activity of the specific compound employed, the age, body weight, general health, sex, diet, time of administration, route of administration, and rate of excretion, drug combination and the severity of the particular disease undergoing therapy.

In an aspect, the additional active agent includes a steroid, an antibacterial, an anti-cancer agent, an anti-parasitic, an anti-fungal, or a combination thereof.

Non-limiting examples of the anti-cancer active agent include abemaciclib, abiraterone acetate, acalabrutinib, ado-trastuzumab emtansine, alemtuzumab, apalutamide, alpelisib, anastrozole, atezolizumab, axicabtagene ciloleucel, azacytidine, belantamab mafodotin-blmf, belinostat, bendamustine hydrochloride, bevacizumab, bleomycin sulfate, bicalutamide, bortezomib, bosutinib, brentuximab vedotin, brexucabtagene autoleucel, bortezomib, busulfan, cabazitaxel, capecitabine, carboplatin, carfilzomib, carmustine, casodex, chlorambucil, cicalutamide, cisplatin, copanlisib hydrochloride, crizotinib, cytarabine, cyclophosphamide, daunorubicin, darolutamide, darubicin, daratumumab, dasatinib, dacarbazine, degarelix, denileukin diftitox, dexamethasone, docetaxel, doxorubicin, doxorubicin hydrochloride, duvelisib, elotuzumab, enasidenib mesylate, enzalutamide, epirubicin hydrochloride, eribulin mesylate, everolimus, exemestane, fam-trastuzumab deruxtecan-nxki, fludarabine phosphate, flutamide, fulvestrant, galetertone, gemtuzumab, gemcitabine hydrochloride, gilteritinib fumarate, glasdegib maleate, goserelin acetate, hydrocortisone, hydroxyurea, ibrutinib, ibritumomab tiuxetan, idecabtagene vicleucel, idelalisib, idecabtagene vicleucel, imatinib mesylate, inotuzumab ozogamicin, isatuximab-irfc, ixazomib citrate, ixabepilone, ivodisenib, ixazomib citrate, lapatinib ditosylate, lenalidomide, letrozole, leuprolide acetate, lisocabtagene maraleucel, lomustine, loncastuximab tesirine-lpyl, 6-mercaptopurine, margetuximab-cmkb, melphalan, melphalan hydrochloride, megestrol acetate, methotrexate, methotrexate sodium, methylprednisolone, midostaurin, mitoxantrone hydrochloride, mogamulizumab-kpkc, nelarbine, nilotinib, neratinib maleate, nilutamide, niraparib tosylate monohydrate, nivolumab, obinutuzumab, ofatumumab, olarparib, omacetaxine mepesuccinate, orteronel, paclitaxel, palbociclib, pamidronate disodium, panobinostat lactate, pamidronate disodium, pembrolizumab, pertuzumab, plerixafor, pralatrexate, procarbazine hydrochloride, pomalidomide, polatuzumab vedotin-piiq, ponatinib hydrochloride, prednisolone, prednisone, relugolix, ribociclib, rituximab, romidepsin, rucarib camsylate, sacituzumab govitecan-hziy, selinexor, sipuleucel-T, tafasitamab-cxix, tamoxifen citrate, tazemetostat hydrobromide, thalidomide, thioguanine, thiotepa, tisagenlecleucel, topotecan hydrochloride, toremifene, trastuzumab, tucatinib, umbralisib tosylate, venetoclax. vinblastine sulfate, vincristine, vincristine sulfate, vorinostat, zanubrutinib, zoledronic acid, VT464, CFG920, TOK-001, and combinations thereof.

Non-limiting examples of the antibacterial active agent include amikacin, bedaquiline, benzothiazinone, capreomycin, ciprofloxacin, clofazimine, cycloserine, delamanid, ethambutol, ethionamide, isoniazid, kanamycin, linezolid, macrolides, ofloxacon, para-amino salicylic acid, pentamidine, pyrazinamide, rifampicin, streptomycin, thioacetazone, viomycin, PA-824, SQ-109, and combinations thereof.

Non-limiting examples of the anti-parasitic and/or anti-fungal active agent include benzothiazinone, pentamidine, suramin, melarsoprol, eflornithine, nifurtimox, fexinidazole, clomitrazole, erconazole, micronazole, terbinafine, fluconazole, ketoconazole, amphotericin, lanosterol 14a-demethylase, benznidazole, nifurtimox, and combinations thereof.

The compositions and methods of treatment disclosed herein are useful for inhibiting the activity of a CYP enzyme in a human, as well as for treatment of mammals other than humans, including for veterinary applications such as to treat horses and livestock, e.g. cattle, sheep, cows, goats, swine and the like, and pets (companion animals) such as dogs and cats.

EXAMPLES

The following examples describe the preparation and characterization of a number of steroid-based isonitrile inhibitors of CYP17A1, a human CYP involved in the synthesis of androgens, and CYP106A2 ($P450_{meg}$), a bacterial P450 capable of steroid oxidations that make it of interest for pharmaceutical manufacture.

The isonitrile compounds described in the present disclosure are derived from a steroid or steroid-like structure, and can be readily synthesized from a molecule having appropriately positioned carbonyl groups. Reaction Schemes 1-3 below show the synthetic pathways used to prepare several different steroid-derived isonitrile compounds that were designed to inhibit CYPs that oxidize steroids.

NMR spectroscopy. All NMR experiments were performed on a Bruker NEO spectrometer operating at 800.13 MHz ($^1$H), 201.19 MHz ($^{13}$C) and 81.08 MHz ($^{15}$N). All $^1$H and $^{13}$C chemical shifts are reported in ppm relative to tetramethylsilane; $^{15}$N shifts are reported in ppm relative to anhydrous ammonia. For assigning $^1$H and $^{13}$C correlations, $^1$H,$^{13}$C-HSQC and HMBC experiments were performed. Formamide $^{15}$N resonances were assigned using natural abundance $^1$H,$^{15}$N-HSQC. Stereochemistry at reaction centers was established by $^1$H,$^1$H NOESY experiments, based on the known stereochemistry of steroid starting materials.

Example 1: 3β-formyl-(R)-(20-amidoformyl)pregnane (Compound 20(R)-2b) and 3β-formyl-(S)-(20-amidoformyl)pregnane (Compound 20(S)-2b)

2 g of 3β-hydroxy-5α-pregnan-20-one 1 (3.2 mmole) (CAS 516-55-2, Oakwood Chemical, Estill SC) was added to 4 mL of 88% formic acid and 4.8 mL of formamide in a Pyrex test tube equipped with a magnetic stir bar. The test tube was stoppered with glass wool and heated to 165° C. on an aluminum heating block with stirring and held at temperature for 3 hours. After cooling, the two-phase mixture was mixed with sufficient benzene to dissolve the solid upper layer. The organic layer was filtered to remove unreacted starting material 1 which is relatively insoluble in benzene, then washed 2× with saturated $NaHCO_3$ solution, dried over anhydrous $Na_2SO_4$, filtered, evaporated and recrystallized from benzene. Reversed phase HPLC of the first crop of the recrystallized material ($C_{18}$ column, acetonitrile/water gradient 20/80->90/10, detection at 210 nm) showed evidence for several products, and $^1$H,$^{13}$C NMR of the isolated fractions confirmed that R and S epimers of the formamide are present in—2:1 proportion. Furthermore, two conformational isomers due to rotation around the N—CO bond were observed at slow exchange for both epimers. Finally, the 3β-hydroxy group was esterified by formic acid in ~70% of the product, based on NMR signal intensities. Melting points of the separated fractions were 185° C. ($20_S$-2b) and 195° C. ($20_R$-2b). The second crop of crystals from benzene resulted in 0.78 g having a melting point of 175-180° C. was determined by NMR to be essentially pure 20(R)-2b and was used for the isonitrile synthesis without Reaction Scheme 1

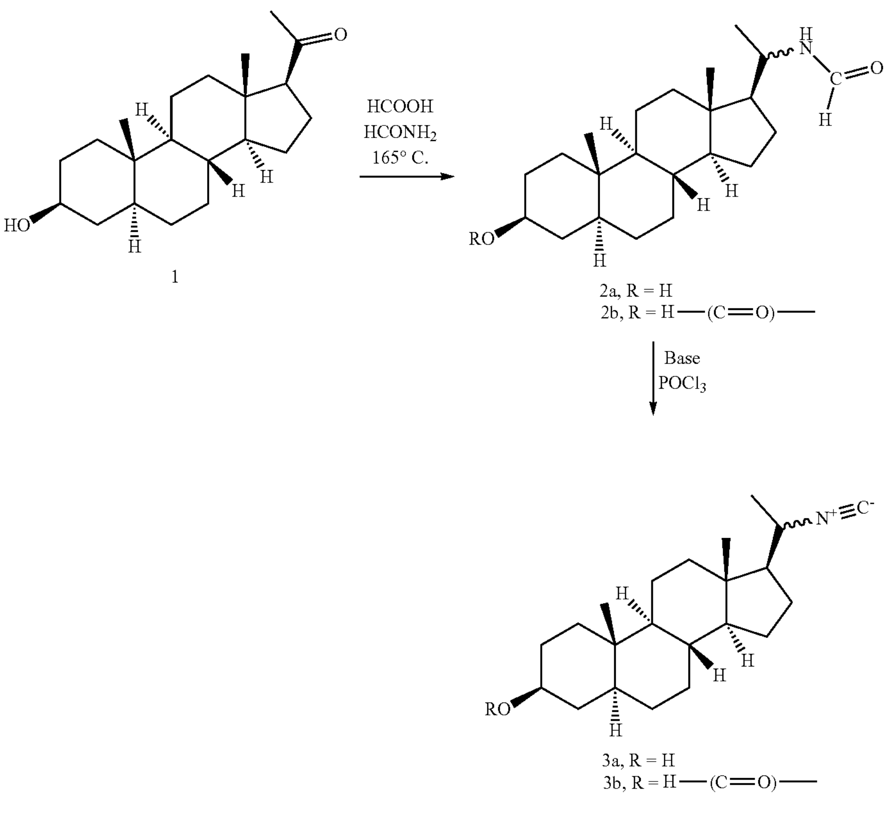

1

2a, R = H
2b, R = H—(C=O)—

3a, R = H
3b, R = H—(C=O)— further purification. The peaks arising from 20(R)-2b and 20(S)-2b are identified below.

$^{1}H$ NMR ($d_6$-benzene): H1 (2a, 0.78, 1.50; 2b, 0.74, 1.50); H2 (2a, 1.48, 1.73; 2b 1.50, 1.77); H3 (2a, 3.43; 2b 4.85); H4 (2a, 1.22, 1.49; 2b 1.31, 1.55); H5 (2a, 0.91, 2b 0.87); H6, 1.07; H7, 0.74, 1.12; H8, ($S_{20}$, 1.13; $R_{20}$ 1.80); H9 (2a, 0.47; 2b 0.44); H11 ($R_{20}$, 1.10, 1.35; $S_{20}$ α, 1.44; $S_{20}$ β, 0.89); H12, 1.74; H14, 2.13; H15 ($R_{20}$α 1.50, $R_{20}$ β, 2.34; $S_{20}$ α, 1.29; $S_{20}$ β, 1.12); H16 ($R_{20}$α 1.03, $R_{20}$β, 1.59; $S_{20}$ α, 1.74; $S_{20}$ β, 0.86); H17 ($R_{20}$, 0.98 $S_{20}$, 1.04); H18 ($R_{20}$, 0.56; $S_{20}$, 0.38); H19 (2a, 0.64; 2b, 0.61); H20 ($R_{20}$, 4.02; $S_{20}$, 2.77); H21 ($R_{20}$, 0.97; $S_{20}$, 0.75).

$^{13}C$ NMR ($d_6$-benzene): C1, 37.2; C2, (2a, 32.3, 2b 28.1); C3, (2a, 71.4, 2b 73.6); C4, (2a, 39.0, 2b 34.7); C5, (2a, 47.7, 2b 45.0); C6, 29.0; C7, 32.5; C8, 35.8; C9, (2a, 54.4, 2b 54.8); C10, 37.4; C11, (2a, 21.6, 2b 24.3); C12, 32.4; C13 (2a, 2b $R_{20}$, 42.9; 2a $S_{20}$, 43.0; 2b $S_{20}$, 45.9); C14, 64.0; C15, ($S_{20}$, 21.6; $R_{20}$, 23.5); C16 ($R_{20}$, 39.5; $S_{20}$, 40.0); C17 ($R_{20}$, 57.0; $S_{20}$, 56.4); C18 ($R_{20}$, 13.8; $S_{20}$, 12.6); C19, 12.5; C20 (R, 45.3; S, 50.4); C21 ($R_{20}$, 22.1; $S_{20}$, 23.3); formamide carbonyl ($R_{20}$, 162.4; $S_{20}$, 163.7).

$^{15}N$ NMR (in $d_6$-benzene): formamide $S_{20}$, 136.0; $R_{20}$, 102.6.

HRMS: 2b: calculated for $C_{23}H_{38}NO_3$ (M+1), 376.2852, observed, 376.2835. Peaks eluted from C18 reverse phase HPLC (acetonitrile/water gradient), 72% ACN and 73% ACN.

Example 2: 3β-formyl-(R)-(20-isonitrilo)pregnane (Compound 3b)

After drying over $P_2O_5$ in a vacuum desiccator, 0.265 mg (0.8 mmol) of recrystallized 2b was dissolved in 0.8 mL (3.2 mM) of dry pyridine under $N_2$ with stirring and cooled in an ice bath. 80 μL (0.8 mmol) of $POCl_3$ (Sigma) was added slowly dropwise. After all of the $POCl_3$ was added, the ice bath was removed, and the reaction allowed to proceed for ~2 h. The reaction mixture slowly darkened, and when no further color change was observed, the reaction was quenched with the addition of ice chips and 1 mL of saturated $NaHCO_3$ solution. The reaction mixture was then dissolved in 10 mL of $Et_2O$, the aqueous layer discarded and the organic layer filtered through anhydrous $Na_2SO_4$. Solvent was removed by a gentle stream of $N_2$ without heating, and excess pyridine removed using a SpeedVac. The resulting solid was examined by IR spectroscopy to confirm the presence of the isonitrile group, which gives a sharp absorption band at 2138 $cm^{-1}$.

$^{1}H$ NMR ($d_6$-benzene): H1, 0.70, 1.43; H2, 1.41, 1.73; H3, 4.79; H4, 1.27, 1.51; H5, 0.85; H6, 1.01, 1.05; H7, 0.69, 1.45; H8, 1.01; H9, 0.32, 0.39; H11, 1.06, 1.30; H12, 0.76, 1.52; H14 ($R_{20}$, 0.81; $S_{20}$, 0.68); H15 ($R_{20}$ α 1.47, $R_{20}$ β, 2.26; $S_{20}$ α, 1.45; $S_{20}$ β, 1.84); H16 ($R_{20}$ α 1.20, $R_{20}$ β, 1.75; $S_{20}$ α, 1.42; $S_{20}$ β, 0.72); H17 ($R_{20}$, 1.19; $S_{20}$, 1.12); H18 ($R_{20}$, 0.50; $S_{20}$, 0.34); H19, 0.56; H20 ($R_{20}$, 2.94; $S_{20}$, 3.11); H21 ($R_{20}$, 0.97; $S_{20}$, 0.75).

$^{13}C$ NMR ($d_6$-benzene): C1, 37.1; C2, 28.1; C3, 73.2; C4, 34.7; C5, 44.9; C6, 28.9; C7, 32.5; C8, 35.4; C9, 54.5; C10, 36.9; C11, 21.4; C12, 32.7; C13 ($R_{20}$, 43.0; $S_{20}$, 42.3); C14 ($R_{20}$, 56.9; $S_{20}$, 56.3); C15 ($R_{20}$, 23.4; $S_{20}$, 26.9); C16 ($R_{20}$, 39.5; $S_{20}$, 39.1); C17 ($R_{20}$, 55.7; $S_{20}$, 55.8); C18 ($R_{20}$, 12.5; $S_{20}$, 12.5); C19, 12.4; C20 (R, 51.0; S, 52.4); C21 ($R_{20}$, 22.2; $S_{20}$, 22.4); isonitrile C($R_{20}$, 159.1; $S_{20}$, 158.1).

$^{15}N$ NMR (in $d_6$-benzene): isonitrile N($R_{20}$, 136.0; $S_{20}$, 102.6).

HRMS: calculated for $C_{22}H_{35}NO_2$(M+1), 358.2747, observed, 358.2741.

Reaction Scheme 2

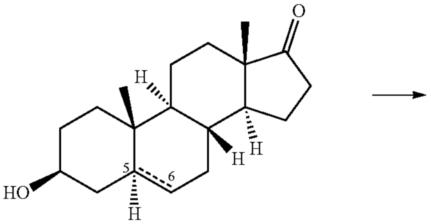

4a, as drawn
4b, $C_5$-$C_6$ dehydro

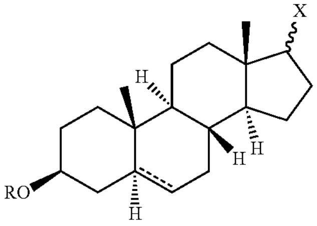

5a, R = H, X = —NH(C=O)H
5b, R = —(C=O)H,
X = —NH(C=O)H
5c, R = H, X = —NH(C=O)H,
$C_5$-$C_6$ dehydro
5d, R = —(C=O)H
X = —NH(C=O)H, $C_5$-$C_6$ dehydro 6a, R = H, X = -NC (isonitrile)
6b, R = —(C=O)H,
X = -NC (isonitrile)
6c, R = H, X = isonitrile, $C_5$-$C_6$ dehydro
6d, R = —(C=O)H
X = isonitrile, $C_5$-$C_6$ dehydro

Example 3: 3β-formyl-(R,S)-(17-amidoformyl)androstane (Compound 5b)

1 g of 3β-hydroxy-5α-androstan-17-one 1 (4a, 2.9 mmole) (CAS 481-29-8, Sigma) was added to 2 mL of 88% formic acid and 2.4 mL of formamide in a Pyrex test tube equipped with a magnetic stir bar. The test tube was stoppered with glass wool and heated to 175° C. on an aluminum heating block with stirring and held at temperature for 4 hours. After cooling, the solid mass was extracted with $CH_2Cl_2$. Considerable high-melting solids remained after $CH_2Cl_2$ extraction, which based on mass balance was likely a polymeric derivative of formamide and formic acid. After removal of from the extract, the product was recrystallized from a minimal amount of ethanol and $CH_2Cl_2$ by slow evaporation. Based on relative NMR signal intensities, the recrystallized product is approximately 95:5 $S_{17}$:$R_{17}$ epimers. Compounds 5a and 5b were separated using reversed phase-HPLC purification (C18 column, gradient elution in acetonitrile and water) and Compound 5b was characterized as summarized below.

$^{1}H$ NMR ($d_6$-benzene): H1, 1.38, 1.59; H2, 1.52, 1.80; H3, 4.77; H4 1.64, 1.69; H5, 1.12; H6, 1.39, 1.77; H7, 0.86, 1.63; H8, 1.32; H9, 0.62; H11, 1.20, 1.51; H12, 0.95, 1.55; H14, ($R_{17}$, 1.03; $S_{17}$ 0.93) H15 ($R_{17}$, 1.15, 1.67; $S_{17}$, 1.17, 1.61); H16 ($R_{17}$, 2.21, 1.29; $S_{17}$, 1.96, 1.22); H17 ($R_{17}$, 3.31; $S_{17}$, 3.10); H18 ($R_{17}$, 0.71; $S_{17}$, 0.64); H19 0.78; formamide 17-HN ($R_{17}$, 7.09; $S_{17}$, 7.15); formamide 17-HCO ($R_{17}$, 7.86; $S_{17}$, 7.93); 3-HCO, 7.96.

$^{13}C$ NMR ($d_6$-benzene): C1, 33.9; C2, 27.3; C3, 73.5; C4, 36.7; C5, 44.5; C6, 31.2; C7, 31.5; C8, 35.5; C9, 54.1; C10, 35.5; C11, 20.5; C12, 36.5; C13 ($R_{17}$, 44.8; $S_{17}$, 42.9); C14 ($R_{17}$, 50.0; $S_{17}$, 52.4); C15 ($R_{17}$, 24.6; $S_{17}$, 23.4); C16 ($R_{17}$, 29.8; $S_{17}$, 28.3); C17 ($R_{17}$, 61.6; $S_{17}$, 63.0); C18 ($R_{17}$, 18.1; $S_{17}$, 11.6); C19, 12.1; formamide carbonyl ($R_{17}$, 165.2; $S_{17}$, 165.1); 3-CHO, 160.9.

$^{15}N$ NMR ($d_6$-benzene): formamide $S_{17}$, 115.6; $R_{17}$, 121.7. HRMS (5a): calculated for $C_{20}H_{34}NO_2$ (M+1), 320.2590, observed, 320.2576.

HRMS (5b): calculated for $C_{21}H_{34}NO_3$ (M+1), 348.2539, observed, 348.2526

Example 4: (R,S)-(17-amidoformyl)androst-5,6-ene (Compound 5c) and 3β-formyl-(R,S)-(17-amido-formyl)androst-5,6-ene (Compound 5d)

1 g of 3β-hydroxy-5α-androst-5,6-ene-17-one 1 (2.9 mmole, CAS 481-29-8, Sigma) was added to 2 mL of 88% formic acid and 2.4 mL of formamide in a Pyrex test tube equipped with a magnetic stir bar. The test tube was stoppered with glass wool and heated to 175° C. on an aluminum heating block with stirring and held at temperature for 6 hours. After cooling, the solid mass was extracted with $CH_2Cl_2$. The product was recrystallized from a minimal amount of hexanes and $CH_2Cl_2$ by slow evaporation, m.p. 255° C. to provide a mixture of Compounds 5c and 5d. Compounds 5c and 5d were separated after recrystallization using reversed phase-HPLC purification (C18 column, gradient elution in acetonitrile and water). NMR showed that the epimer ratio of 5d was greater than 9:1 $S_{17}$ to $R_{17}$.

Compound 5c: HRMS: calculated for $C_{20}H_{32}NO_2$ (M+1), 318.2433, observed, 318.2417.

Compound 5d: $^1H$ NMR (d-chloroform): H1, 1.16, 1.89; H2 1.65, 1.90; H3, 4.73; H4, 2.35; H6, 5.40; H7, 1.58, 2.01; H8, 1.32; H9, 1.16; H11, 1.35, 1.63; H12, 1.08, 1.75; H14, ($R_{17}$, 1.05; $S_{17}$ 1.13); H15 ($R_{17}$, 1.44, 1.61; $S_{17}$, 1.40, 1.58); H16 ($R_{17}$ α 1.51, $R_{17}$ β, 2.09; $S_{17}$ α, 1.36; $S_{17}$ β, 2.14); H17 ($R_{17}$, 3.26; $S_{17}$, 3.97); H18, 0.73; H19, 1.04; formamide 17-HN ($R_{17}$, 6.10; $S_{17}$, 5.56); formamide 17-HCO ($R_{17}$, 8.03; $S_{17}$, 8.20); 3-HCO, 8.04; $^{13}C$ NMR (d-chloroform): C1, 36.9; C2, 27.5; C3, 73.8; C4, 42.2; C5, 139.4; C6, 122.6; C7, 31.5; C8, 35.4; C9, 53.9; C10, 37.32; C11, 20.25; C12, 36.2; C13 ($R_{17}$, 42.8; $S_{17}$, 42.9); C14 ($R_{17}$, 52.8; $S_{17}$, 52.8); C15 ($R_{17}$, 20.4; $S_{17}$, 20.5); C16 ($R_{17}$, 28.8; $S_{17}$, 28.6); C17 ($R_{17}$, 62.6; $S_{17}$, 57.5); C18, 11.7; C19, 19.12; formamide carbonyl ($R_{17}$, 164.2; $S_{17}$, 161.2); 3-CHO, 160.4; $^{15}N$ NMR (d-chloroform): formamide $S_{17}$, 114.3; $R_{17}$, 112.8; HRMS: calculated for $C_{21}H_{32}NO_3$ (M+1), 346.24382, observed, 346.2365.

Example 5: Compound 6a was synthesized according to the method described in Example 2, using Compound 5a as the starting material. Compound 6a was purified by reverse-phase HPLC (C18 column) and eluted with 95% acetonitrile via gradient elution (0%-100% acetonitrile/water).

HRMS (calculated for $C_{20}H_{32}NO$ (M+1), 302.2484, observed 302.2465).

Example 6: Compound 6b was synthesized according to the method described in Example 2, using Compound 5b as the starting material. Compound 6b was purified by reverse-phase HPLC (C18 column) and eluted with 95% acetonitrile via gradient elution (0%-100% acetonitrile/water).

$^1H$ NMR ($d_6$-DMSO): $S_{17}$ H, 3.43; $^{13}C$ NMR ($d_6$-DMSO): $S_{17}$ C17, 70.0; $S_{17}$ N$\underline{C}$, 156.3 (broad); HRMS: calculated for $C_{21}H_{32}NO_2$ (M+1), 330.2433, observed 330.2417.

Example 7: Compound 6a was synthesized according to the method described in Example 2, using Compound 5c as the starting material. Compound 6a was purified by reverse-phase HPLC (C18 column) and eluted with 82% acetonitrile via gradient elution (0%-100% acetonitrile/water).

HRMS: calculated for $C_{20}H_{30}NO$ (M+1), 300.2323, observed 300.2308.

Example 8: 7-isonitrilo-DHEA (7c) was prepared according to the Reaction Scheme 3. The synthetic details are similar to the methods described in Examples 1-2, except that a starting material was used. The 7-isonitrilo-DHEA was purified by HPLC (C18 column) and eluted at 58% acetonitrile via gradient elution (0%-100% acetonitrile/water).

Reaction Scheme 3.

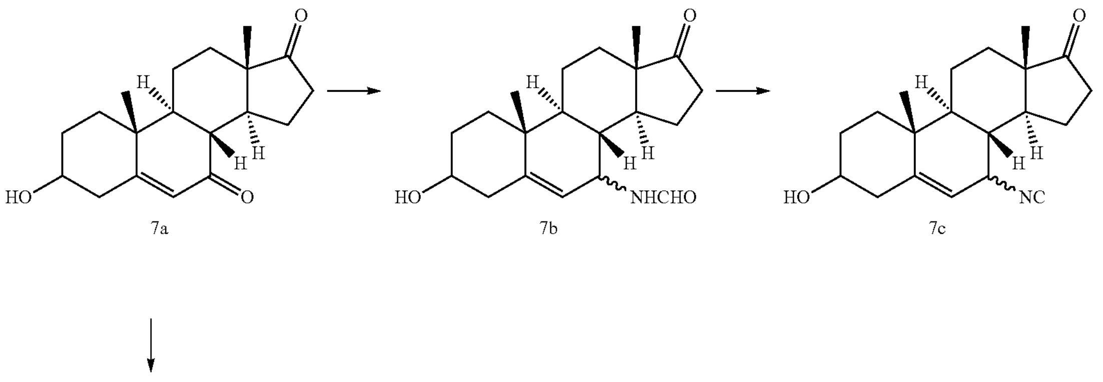

7a 7b 7c

-continued

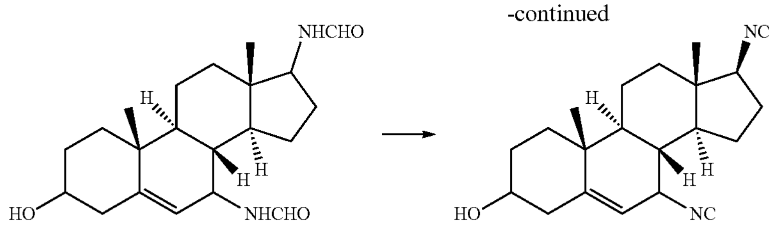

7d 7e

HRMS: Calculated for $C_{20}H_{28}NO_2$ (M+1), 314.2120, found 314.2105.

Example 9: Compound 7e (3β-formyl-5,6-dehydro-7(R, S)-17(S)-diisonitriloandrostene) was prepared similarly to Examples 1-4, starting from androstene-30-hydroxy-5,6-dehydro-7,17-dione (7a, CAS 566-19-8, Steraloids, Inc., Newport, RI). The crude 7,17-diformamide 7d was dried over $P_2O_5$ under vacuum and used to prepare the isonitrile 7e without further purification. The presence of the isonitrile was confirmed by IR spectroscopy, with a strong absorption band at 2138 $cm^{-1}$.

Example 10: Assays

The following compounds were tested in the assays described below.

16

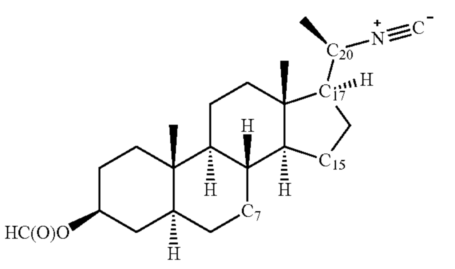

17

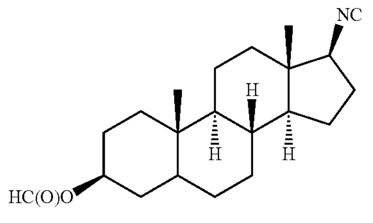

18

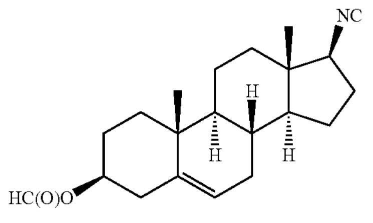

19

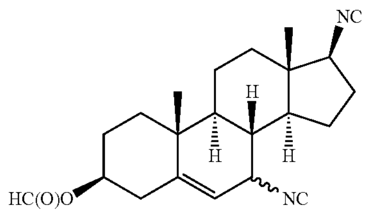

Ligand binding assays. (Adapted from DeVore, N M, et al. (2009). *Drug Metabolism and Disposition,* 37(6), 1319-1327.) Ligand interaction with the heme iron was evaluated by titrating ligands into a cuvette containing purified CYP17A1, CYP2D6, or CYP3A4 and measured using a UV-visible scanning spectrophotometer. Enzyme was diluted to 1 μM in 100 mM potassium phosphate buffer (pH 7.4), 20% glycerol, and 100 mM sodium chloride and divided equally between two 1 mL quartz cuvettes, except for CYP17A1 interacting with 1c, in which the enzyme was diluted to 0.2 μM and divided between two 5 mL cuvettes to evaluate high-affinity binding. Ligands dissolved in DMSO were added to the sample cuvette and an equal volume of DMSO to the reference cuvette. Difference spectra were recorded from 300-500 nm after equilibration of enzyme and ligand. Binding to the enzyme was measured as the difference in maximal and minimal absorbance: $A_{387}$-$A_{419}$ for pregnanolone and 3-formyl pregnanolone, and $A_{435}$-$A_{393}$ for 3-formyl pregnanolone-20-isonitrile with CYP17A1; $A_{434}$-$A_{414}$ for 3-formyl pregnanolone-20-isonitrile with CYP3A4 and CYP2D6. The dissociation constant and maximum spectral change were calculated using a one-site specific binding equation ($Y=B_{max}*X/(K_d+X)$), however, due to the high-affinity binding between CYP17A1 and 1c, the dissociation constant can only be estimated, similar to that of abiraterone. All data fitting was accomplished using GraphPad Prism 9.

Reduction and reoxidation assays. Reduction of the isonitrile-bound P450 complex was observed by taking a baseline absorbance reading from 400 to 500 nm using a UV-visible scanning spectrophotometer, of a 1 cm quartz cuvette containing 1 μM P450, with the selected isonitrile compound at a saturating concentration (i.e., ≥concentration needed to reach $\Delta A_{max}$), in the same buffer used for binding assays (100 mM potassium phosphate buffer (pH 7.4), 20% glycerol, and 100 mM sodium chloride). A small quantity of sodium dithionite (spatula tip-full) was then added to the cuvette, and the spectra were recorded periodically over time to observe the formation of peaks indicating the reduction (~426 and 456 nm) and subsequent reoxidation (~435 nm) of the complex. The total time course for FIG. 6B was 103 minutes and 37 seconds.

Inhibition assays. (Adapted from DeVore, NM, Scott, EE. (2012). *Nature,* 482(7383), 116-119.) Metabolic activity of CYP17A1 was evaluated by measuring 17α-hydroxylation of progesterone as detected HPLC with UV detection at 240 nm. A 1:4 ratio of CYP17A1 to recombinant NADPH-cytochrome P450 reductase was mixed and incubated on ice for 20 minutes. This mixture was added to buffer (50 mM Tris, pH 7.4, 5 mM $MgCl_2$) containing 11.5 μM progesterone and either abiraterone (0-1 μM) or 1c (0-50 μM). Reaction vials were warmed to 37° C. for three minutes, then catalysis was initiated by adding NADPH to a final concentration of 1 mM. After 10 minutes, metabolism was quenched by adding 300 μL of 20% trichloroacetic acid and placed on ice. The reaction vials were centrifuged to pellet the precipitated protein, then the supernatant was injected onto a C18 column (Phenomenex, Luna, 50×4.6 mm) for HPLC. The 30-minute HPLC method ran at 0.8 m/min and started with a mobile phase of 60% acetonitrile, 40% water with 0.2% acetic acid for five minutes, increased to 80% acetonitrile over 10 minutes, held at 80% acetonitrile for five minutes, 100% acetonitrile for five minutes, then returned to 60% acetonitrile to prepare for the next sample. Metabolite elution was normalized to β-estradiol as an internal standard. A standard curve of known product concentrations was used to convert normalized area under curve to amount of product produced. A four-parameter variable-slope equation ($Y=Y_{min}+(Y_{max}-Y_{min})/(1+(IC_{50}/X)$^(Hill Slope))) was used to fit the data and calculate $IC_{50}$ values for inhibitors using GraphPad Prism 9.

Binding Analysis

Isonitrile 3b, derived from 3-hydroxypregnanalone, was designed to inhibit CYP17A1, a target for chemotherapy of prostate cancer. Isonitriles of type 6, were derived from steroids andronstan-17-one and 5,6-dehydroandrosten-17-one.

Figure 3A:
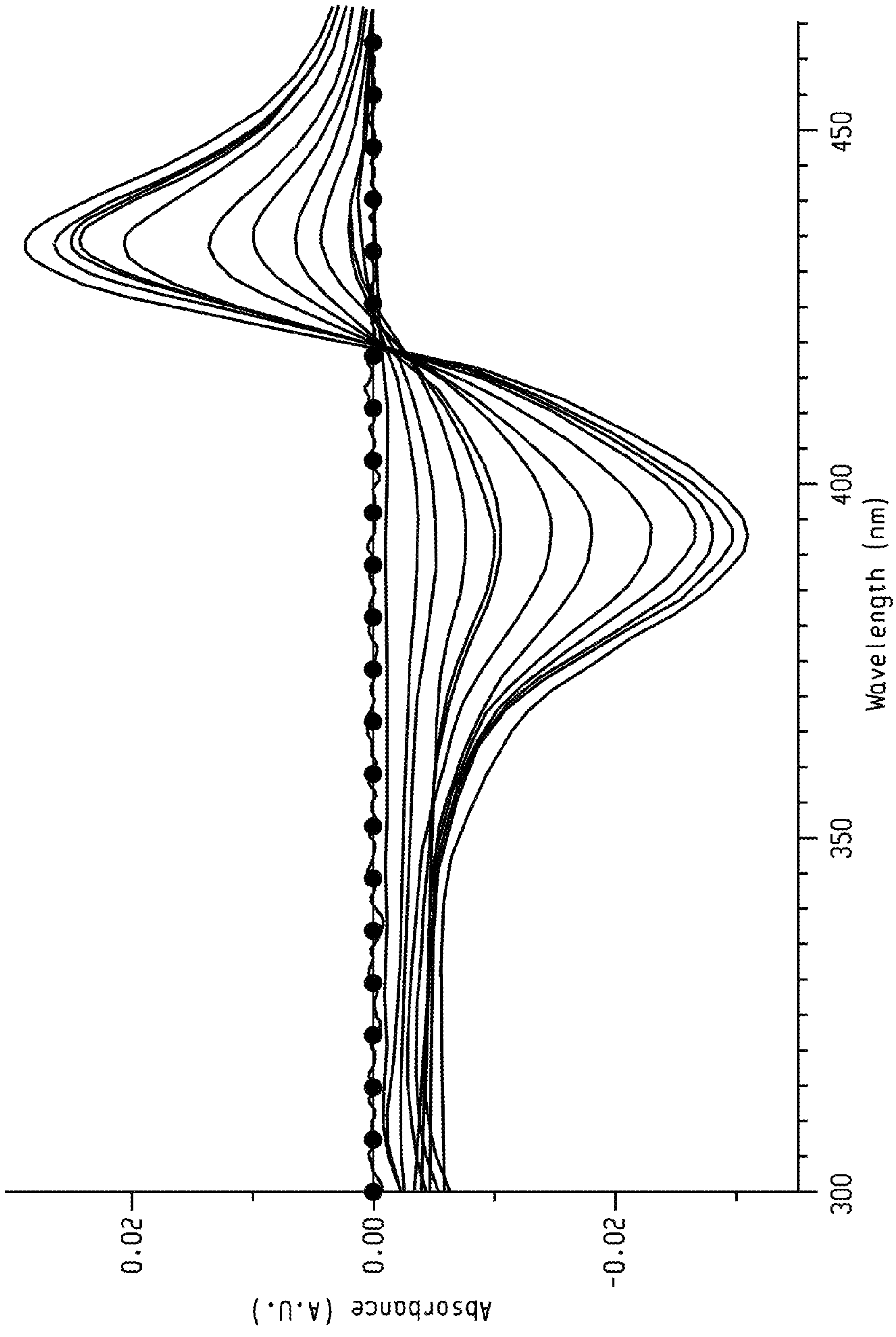
FIGS. 3A-3C show the optical difference spectra when various compounds are titrated with CYPs.
Figure 3B:
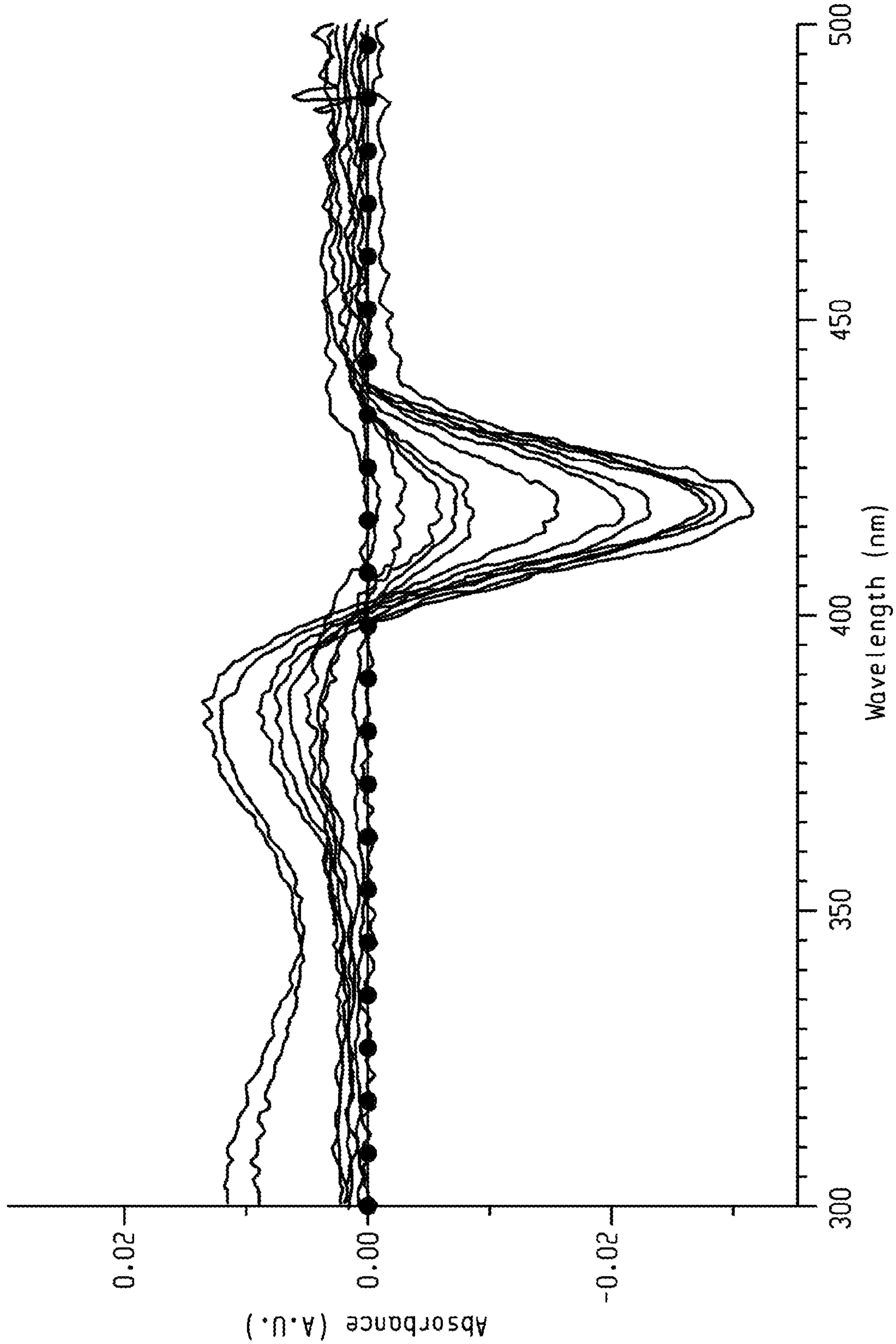
Figure 3C:
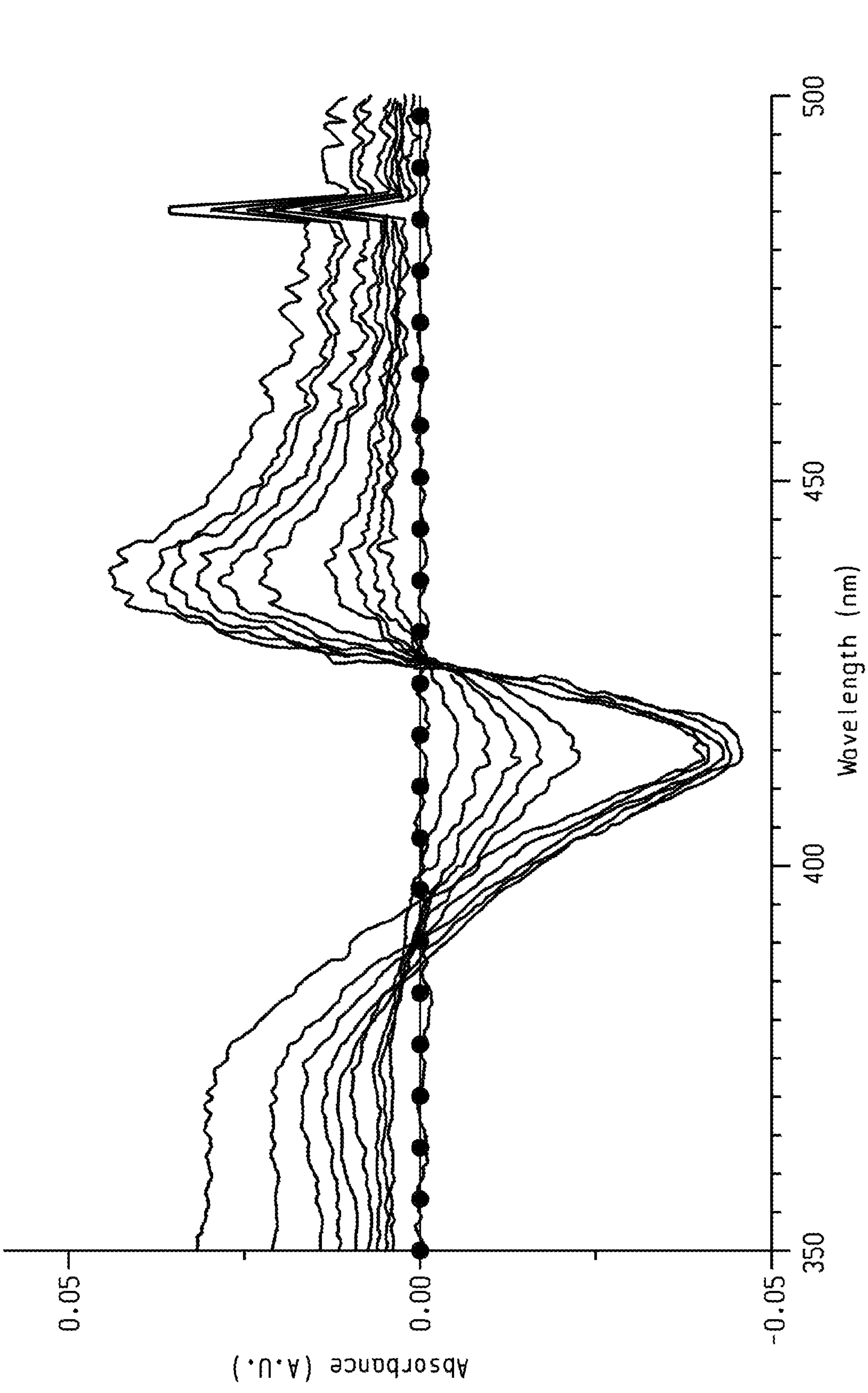
Figure 4:
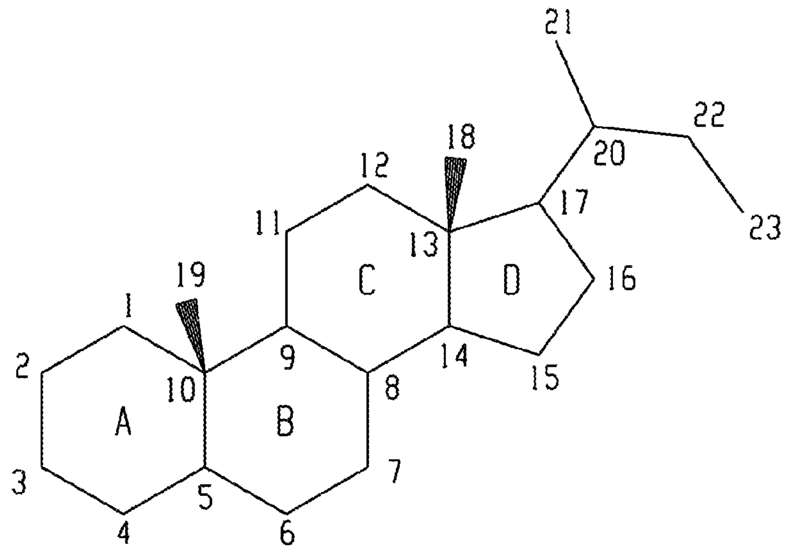
FIG. 4 shows an exemplary steroid structure with the generally acceptable (i.e., IUPAC) numbering for the carbons. Substituents of the steroid ring structure that are above the plane of the ring (e.g., C-10 methyl and C-13 methyl) are referred to as R and those substituents that are below the plane of the ring (not shown) are referred to as u.

As shown in FIGS. 3A and 3B, compound 3b binds tightly to CYP17A1, while compound 6 did not show any spectroscopic evidence of binding to CYP17A1. On the other hand, compound 3 showed no evidence of binding to CYP106A2, another steroid-oxidizing enzyme that exhibits considerably different regiospecificity in its oxidation products than CYP17A1, while compound 6 does show (relatively weak) binding to CYP106A2. It is expected that screening of other steroid-derived isonitriles with greater similarity to the regiospecificity of CYP106A2 will result in isonitriles that bind more tightly to that enzyme. However, the lack of cross-inhibition between these two enzyme-inhibitor pairs demonstrate the possibility of reduced cross-reactivity (and off-target effects) of isonitrile-derived chemotherapeutic agents.

Of compounds 16-19, only compound 16 induced the expected heme spectral shift from 417 to 428 nm that results from formation of a ferric iron-isonitrile dative bond when introduced to CYP17A1. Compounds 17 and 18 were added to 25- and 20-fold molar excess, respectively, and only 17 induced a shift to 420 nm, which is not consistent with isonitrile-heme coordination.

Compound 16 was originally prepared from a 2:1 mixture of C20 epimers of the formamide precursors (see supplementary information). The resulting 2:1 mixture of 16 bound to CYP17A1 as evidenced by a difference spectrum with a Soret peak shifted to 430 nm, indicative of a Fe—CN bond. A single isomer of the formamide precursor was subsequently generated by recrystallization and the isonitrile generated from it bound to CYP17A1 with the same spectral shift and with even higher affinity (FIG. 3A). Thus, stereochemistry of the compound near the heme-ligating isonitrile is also important in optimal binding affinity.

Figure 5A:
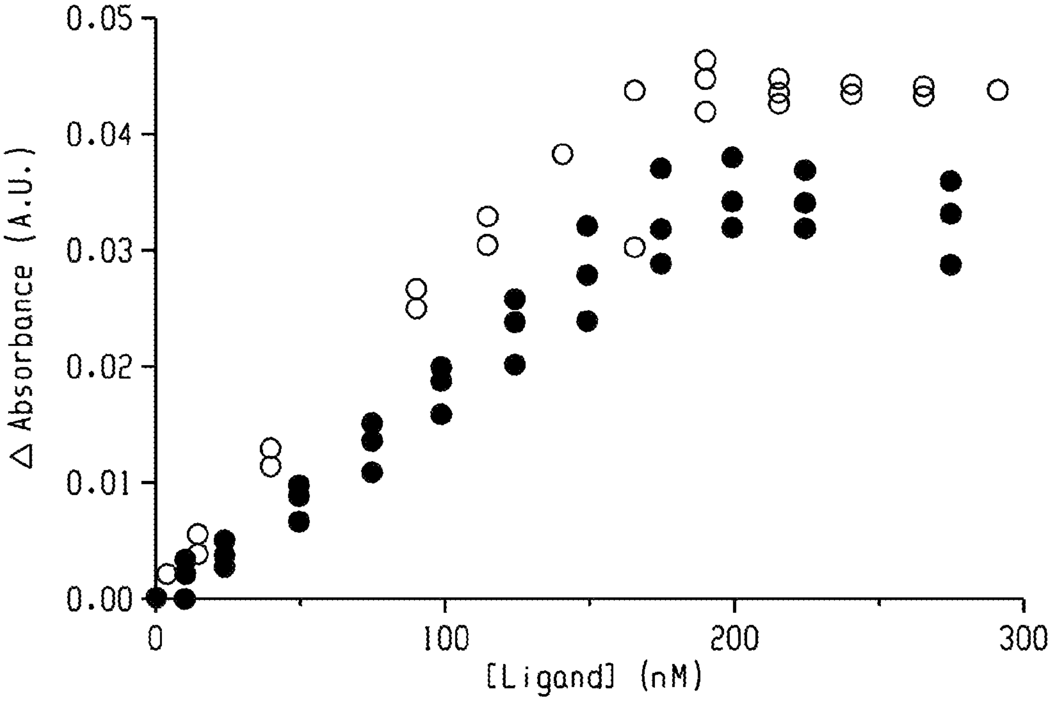
FIGS. 5A-5B show the binding and inhibition of CYP17A1 (0.2 μM) with isonitrile 16 compared to abiraterone.
Figure 5B:
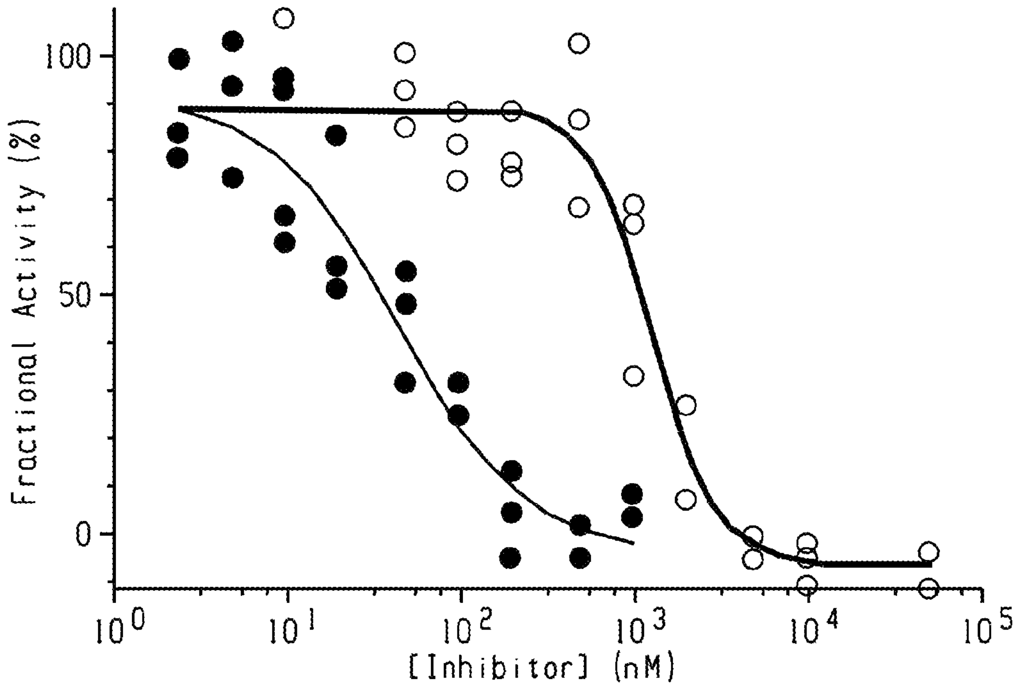

Binding was compared to abiraterone, which is used pharmaceutically as a first-line treatment of prostate cancer and forms a type II Fe—N interaction as evidenced by a shift of the Soret peak to 424 nm. Titration curves revealed both compounds are similarly tight binding (FIG. 5A), with complete saturation by the time the ligand concentration equals protein concentration, yielding only estimates of <100 nM for $K_d$. However, comparison of inhibition by these two compounds yielded an $IC_{50}$ for abiraterone 27-fold lower (47 nM) than for 16 (1300 nM) (FIG. 5B). This may be due to the steric constraints imposed by the linearity of the Fe—CN bond, with optimum Fe—C—N and C—N—R bond angles of 180°. In contrast, the Fe-pyridinyl N bond formed with abiraterone is afforded more flexibility in terms of the rotation of the pyridine ring with respect to the remainder of the molecule.

Figure 7A:
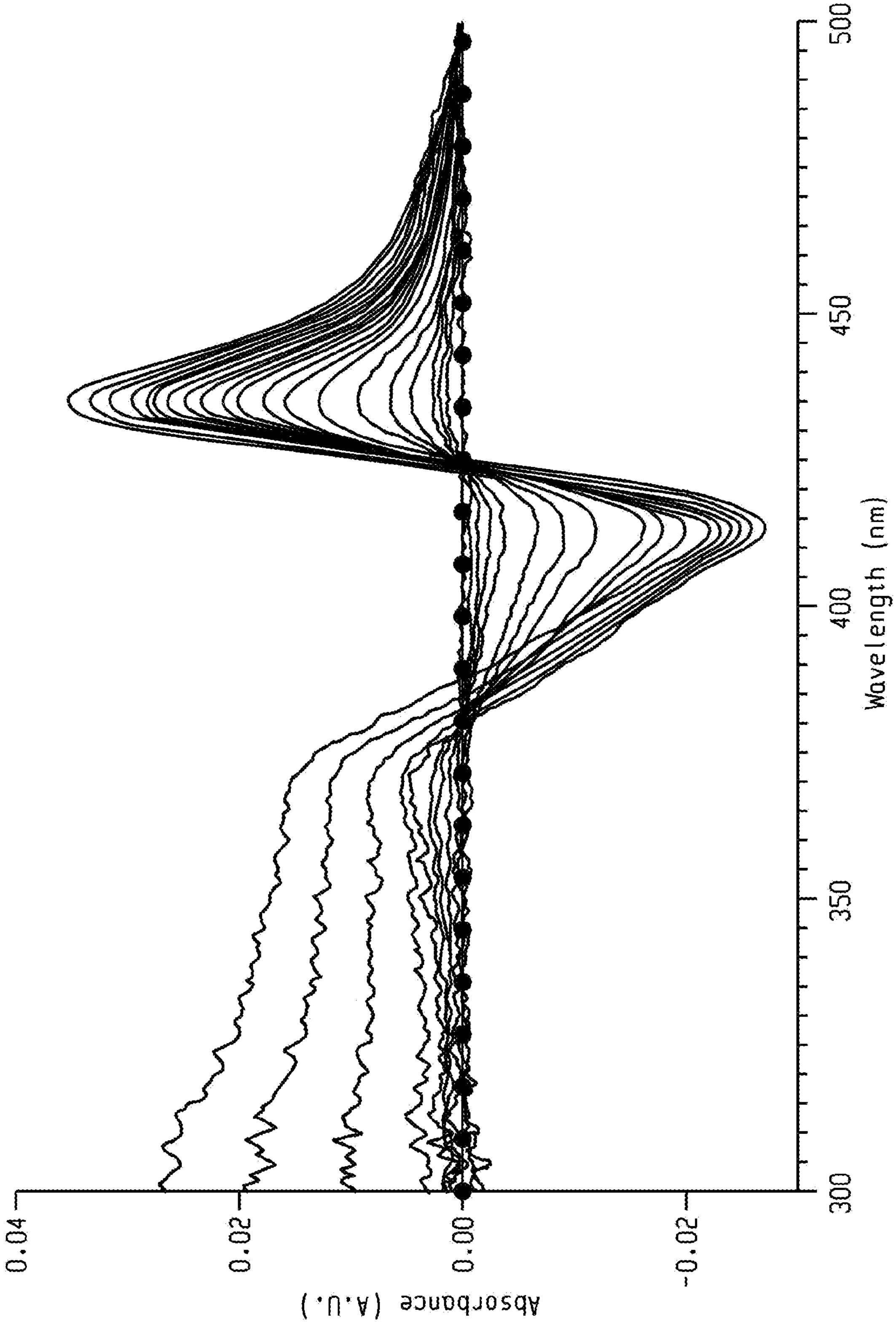
Figure 7B:
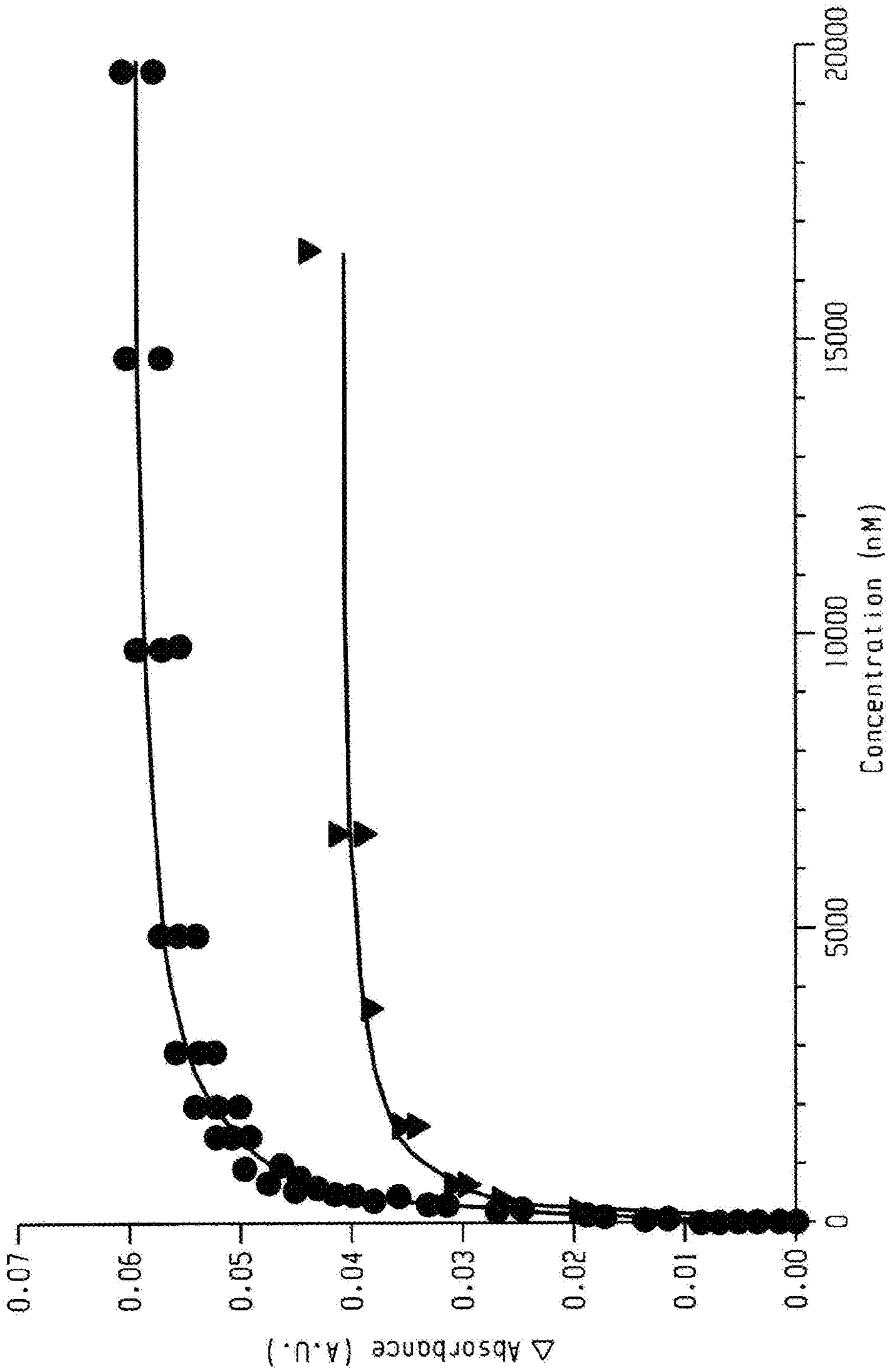

To evaluate the selectivity of 20-(R)-16, this compound was also titrated against other cytochrome P450 enzymes, including the two most prevalent drug-metabolizing P450 enzymes in humans, CYP3A4 and CYP2D6. CYP3A4 is known to have a large and flexible active site so it is perhaps not surprising that titration of CYP3A4 with 20-(R)-16 yields a Soret shift to 434 nM indicating Fe—CN—R bond formation (FIG. 7A). However, the dissociation constant (300 nM) is at least 3-fold higher than for CYP17A1. Contribution of the isonitrile to affinity is apparent in that the parent steroid from which 20-(R)-16 is derived, 3b-formyl-5a-pregnanalone, exhibits a 10-fold higher $K_d$ of ~3200 nM for CYP3A4 (data not shown). Titration of CYP2D6 with 20-(R)-16 also indicated the formation of the Fe—CN—R bond (not shown) with a dissociation constant in the same range (250 nM) as CYP3A4 (FIG. 7B).

Figure 8:
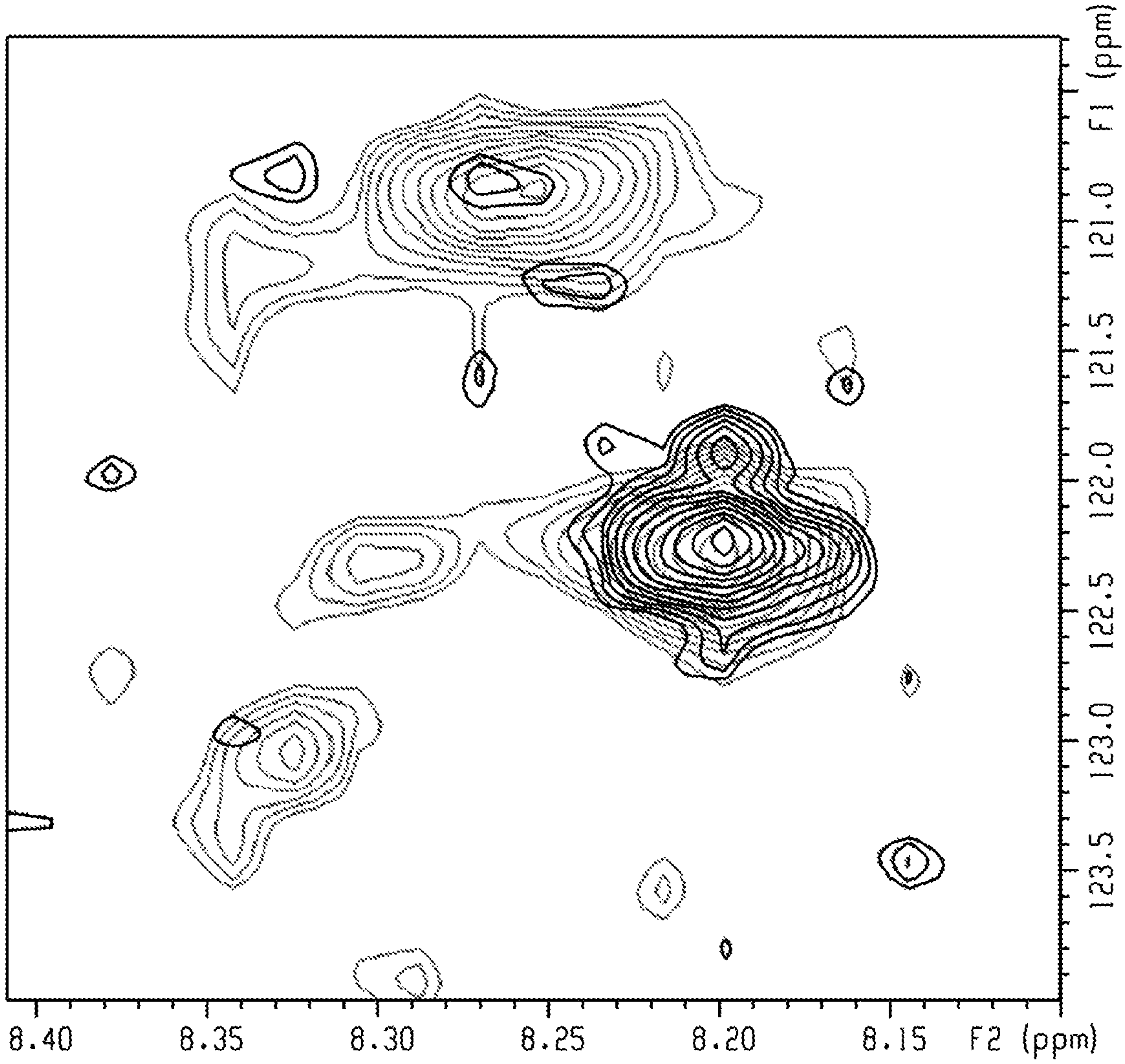
FIG. 8 shows the overlay of 800 MHz $^1H$,$^{15}N$-TROSY-HSQC spectra of $^{15}N$-Gly-labeled CYP106A2 with levopimaric acid p-benzoquinone Diels-Alder adduct bound after reduction with sodium dithionite and treatment with carbon monoxide (heavier-weight lines), or with 7,17-(bis)isonitrile 19 (lighter-weight lines) after reduction with sodium dithionite.

Unlike the human cytochrome P450 enzymes evaluated above, 20-(R)-16 shows no evidence for formation of a Fe—CN—R bonded complex with the bacterial steroidogenic CYP106A2. Instead, 17 results in a weak type I (substrate-like) blue shift of the Soret peak (FIG. 3B). While CYP17A1 hydroxylates steroids at C17, CYP106A2 hydroxylates steroids at C15 and C7.[13] Therefore a bis-isonitrile with and additional isonitrile at C-7 (19) was prepared. The crude product does form an iron-isonitrile bond upon binding to CYP106A2 (FIG. 3C). Thus, the proximity of the isonitrile functionality to the oxidized position(s) is likely important in determining whether an iron-isonitrile bond forms. As expected, the CYP106A2/19 complex could be reduced to form a stable diamagnetic complex suitable for NMR (see FIG. 8).

Example 11: Protein Crystallization and Structure Determination

CYP17A1 was saturated with 3β-formyl-5α pregnanolone-20(R)-isonitrile (verified by 430 nm Soret peak) and using hanging drop vapor diffusion. A protein solution of 30 mg/mL CYP17A1 in 50 mM Tris-HCl (pH 7.4), 20% glycerol, 500 mM NaCl, and 0.2% Emulgen 913 was equilibrated against 0.1 M Tris-HCl (pH 8.5), 0.25 M $LiSO_4$, 30% PEG 3350, and 7% sucrose at 22 degrees C. Crystals appeared after 48 hours. Crystals were cryoprotected in mother liquor supplemented with 24% glycerol and flash cooled in liquid nitrogen. Diffraction data was collected at 100 K at the Stanford Synchrotron Radiation Laboratory beamline 12-2. Data were processed to 2.2 Angstroms using XDS Kabsch, W. XDS. *Acta crystallographica. Section D, Biological crystallography* 2010, 66 (Pt 2), 125-132. DOI: 10.1107/S0907444909047337) and Scala (Evans, P. Scaling and assessment of data quality. *Acta Crystallogr D Biol Crystallogr* 2006, 62 (Pt 1), 72-82. DOI: 10.1107/S0907444905036693 From NLM Medline). The structure was solved by molecular replacement using PHASER (McCoy, A. J.; Grosse-Kunstleve, R. W.; Adams, P. D.; Winn, M. D.; Storoni, L. C.; Read, R. J. Phaser crystallographic software. *Journal of applied crystallography* 2007, 40 (Pt 4), 658-674. DOI: 10.1107/S0021889807021206) with a search model based on CYP17A1 complexed with 3-keto-5α-abiraterone (PDB 6WW0). Iterative model building and structure refinement were accomplished using COOT (Emsley, P.; Lohkamp, B.; Scott, W. G.; Cowtan, K. Features and development of Coot. *Acta crystallographica. Section D, Biological crystallography* 2010, 66 (Pt 4), 486-501. DOI: 10.1107/S0907444910007493) and Phenix.refine (Adams, P. D.; Afonine, P. V.; Bunkoczi, G.; Chen, V. B.; Davis, I. W.; Echols, N.; Headd, J. J.; Hung, L. W.; Kapral, G. J.; Grosse-Kunstleve, R. W.; et al. PHENIX: a comprehensive Python-based system for macromolecular structure solution. *Acta crystallographica. Section D, Biological crystallography* 2010, 66 (Pt 2), 213-221. DOI: 10.1107/50907444909052925). Validation of this structure was performed in Phenix. All figures were made using PyMOL (*The PyMOL Molecular Graphics System;* Schrodeinger, LLC: New York, 2017).

Figure 6:
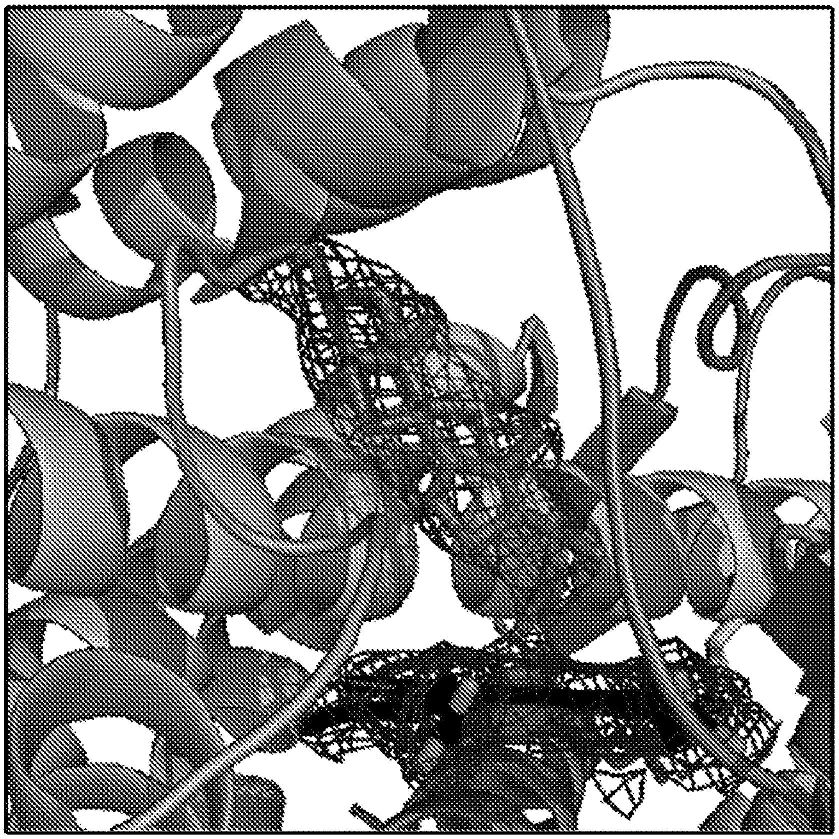
FIG. 6 shows a crystal structure of CYP17A1 with the isonitrile substituent of 20-(R)-16 coordinating to the heme iron. Electron density (2Fo-Fc map) is indicated in mesh for the ligand and heme.

Co-crystallization of CYP17A1 with the tighter-binding epimer of 16 revealed that this is the 20-(R) epimer and confirmed formation of the Fe—CN bond. The crystal structure is shown in FIG. 6.

Example 12: Reduced Cytochrome P450 Interactions with Steroidal Isonitriles

Figure 9A:
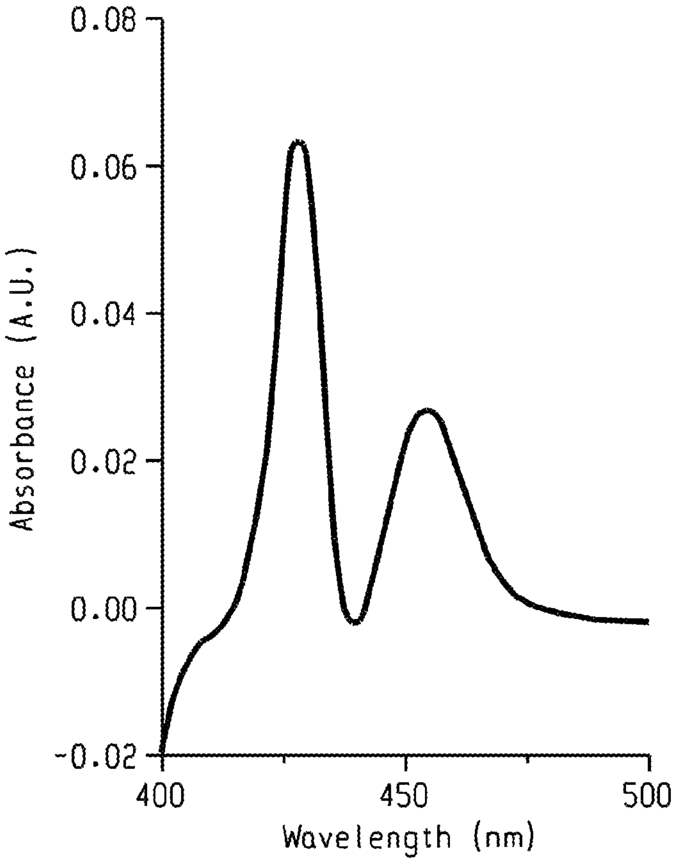
FIGS. 9A-9B show the absorbance spectra of the reduced cytochrome P450 enzymes with 20-(R)-16 bound.
Figure 9B:
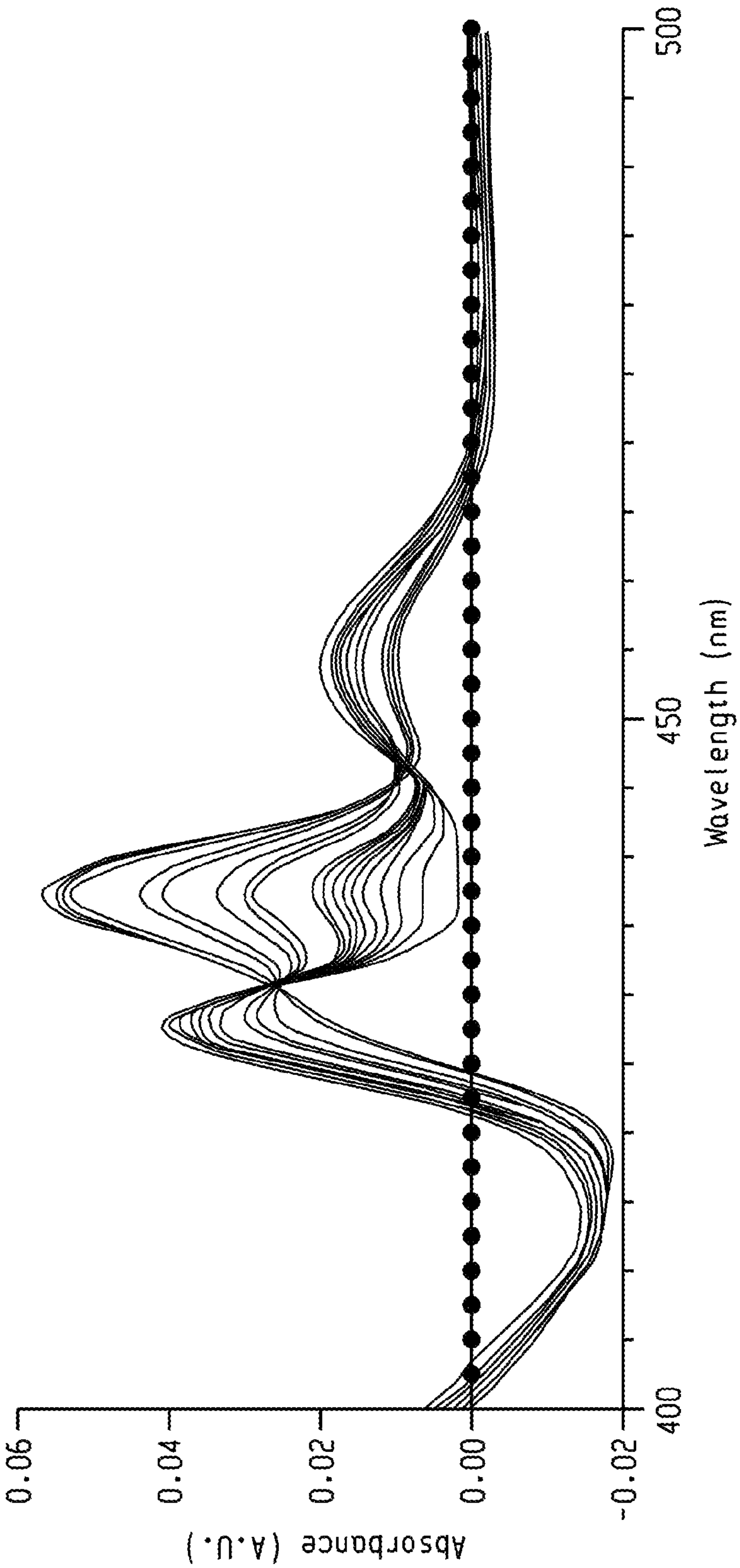

A significant advantage of isonitrile-based P450 inhibitors is their ability to bind both oxidation states. Reduction of the CYP17A1/20-(R)-16 complex gives rise to a distinctive Soret doublet[8] with absorbance at 430 and 455 nm (FIG. 9A). Evidence of the stability of the reduced isonitrile complex was investigated with CYP3A4. Oxidized CYP3A4 saturated with 20-(R)-16 was reduced with sodium dithionite and then allowed to re-oxidize in air (FIG. 9B). Reappearance of the oxidized Fe—CN 435 nm peak and isosbestic points at 430 and 445 nm indicate a clean two-state conversion between the reduced and oxidized complexes with the isonitrile still bound.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A compound or a pharmaceutically acceptable salt thereof, wherein the compound is selected from:

3a

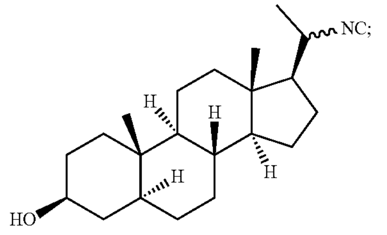

3b

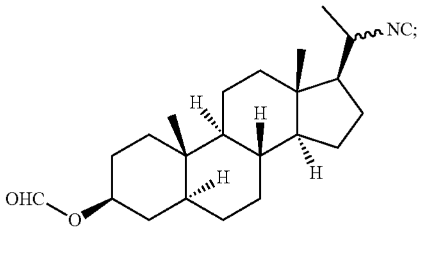

-continued

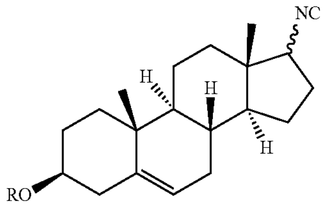

6d: R = H;
6e: R = CHO;
6f: R = acetyl;

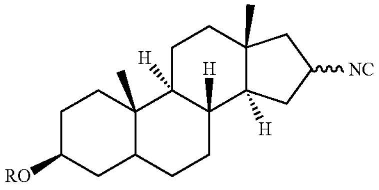

6a-16: R = H;
6b-16: R = CHO;
6c-16: R = acetyl;

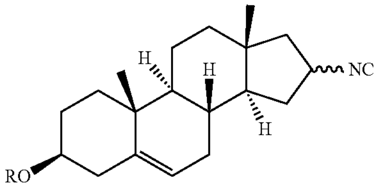

6d-16: R = H;
6e-16: R = CHO;
6f-16: R = acetyl;

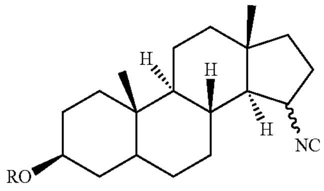

6a-15: R = H;
6b-15: R = CHO;
6c-15: R = acetyl;

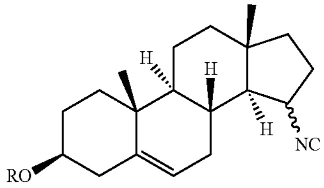

6d-15: R = H;
6e-15: R = CHO;
6f-15: R = acetyl;

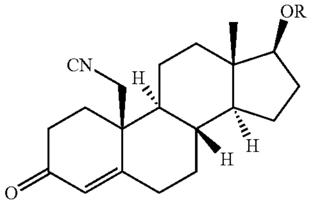

10a: R = OH;
10b: R = CHO;
10c: R = acetyl;

-continued

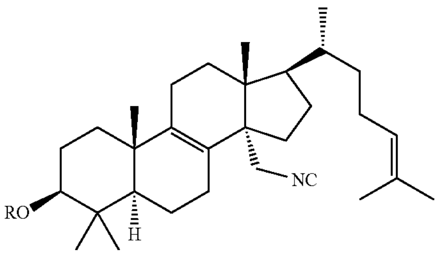

11a: R = OH;
11b: R = CHO;
11c: R = acetyl;

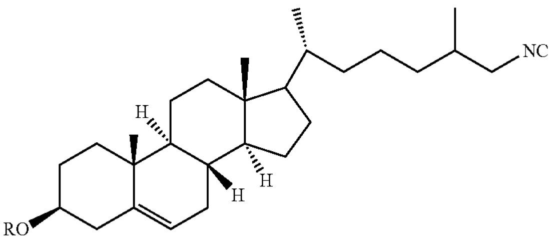

12a: R = OH;
12b: R = CHO;
12c: R = acetyl;

13a

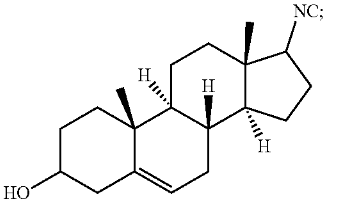

13b

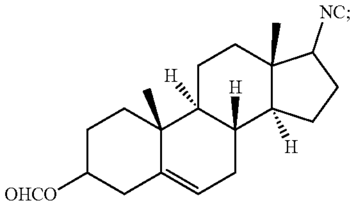

14a

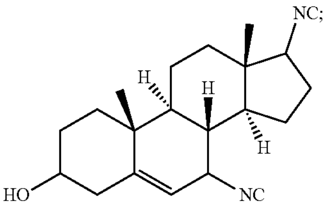

14b

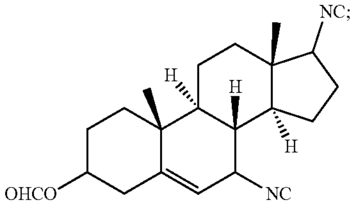

-continued

15a

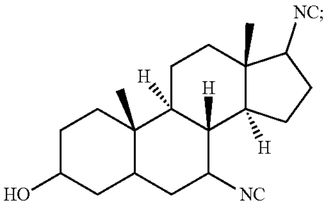

15b

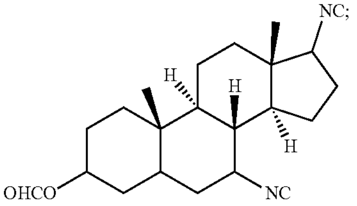

16

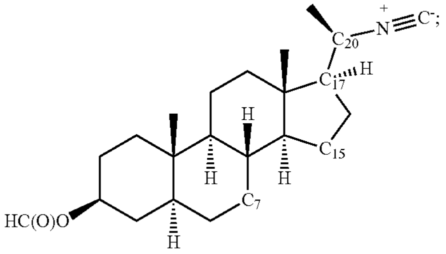

17

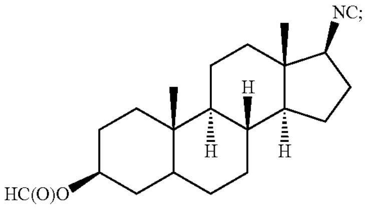

18

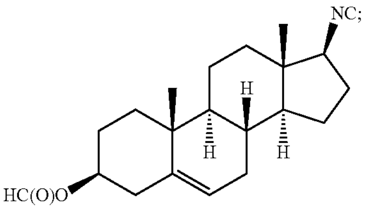

and

19

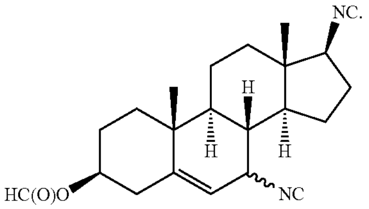

2. A pharmaceutical composition comprising the compound of claim 1 or a pharmaceutically acceptable salt thereof, and a pharmaceutically acceptable carrier and optionally comprising an additional active agent.

3. The pharmaceutical composition of claim 2, wherein the additional active agent comprises a steroid, an antibacterial agent, an anti-cancer agent, an anti-parasitic agent, an anti-fungal agent, or a combination thereof.

4. A composition comprising:

a plurality of encapsulated nanoparticles, wherein each of the nanoparticles independently comprises a core comprising the compound of claim 1 or a pharmaceutically acceptable salt thereof, and an outer shell at least partially encapsulating the core, and a targeting moiety linked to the outer shell, wherein the targeting moiety comprises a protein, a nucleic acid, a nucleic acid analog, a carbohydrate, an antibody, a small molecule, or a combination thereof.

5. A method for targeted delivery of a cytochrome P450 (CYP) inhibitor to a target region in a subject in need thereof, wherein the target region is a cell, tissue, organ, or organ system to which the targeting moiety binds, and the method comprises administering the composition of claim 4 to the subject.

6. The method of claim 5, wherein the subject has a steroid-resistant cancer and the target region is a tumor.

7. A method of inhibiting activity of a cytochrome P450 (CYP) in a subject having a steroid-responsive cancer, an antibiotic-resistant *Mycobacterium tuberculosis* infection, a fungal infection, or a trypanosome infection, the method comprising administering to the subject the compound of claim 1 or a pharmaceutically acceptable salt thereof, in an amount effective to inhibit the CYP activity in the subject.

8. The method of claim 7, wherein the subject has a steroid-responsive cancer and the CYP comprises CYP17A1.

9. The method of claim 7, wherein the subject has an antibiotic-resistant *Mycobacterium tuberculosis* infection and the CYP comprises CYP124A1, CYP125A1, CYP142A1, or a combination thereof.

10. A method of treating a steroid-responsive cancer in a subject comprising administering to the subject the compound of claim 1 or a pharmaceutically acceptable salt thereof, in an amount effective to treat the steroid-responsive cancer in the subject . . .

11. The method of claim 10, wherein the steroid-responsive cancer is prostate cancer, acute lymphoblastic leukemia, acute myeloid leukemia, chronic lymphocytic leukemia, chronic myeloid leukemia, Hodgkin's lymphoma, non-Hodgkin's lymphoma, multiple myeloma, breast cancer, ovarian cancer, or a combination thereof.

12. A method providing a chemical structure of an isonitrile inhibitor of a cytochrome P450 comprising (a) oxidizing a parent compound with a cytochrome P450 to provide an oxidation product comprising an oxidized functional group; (b) determining a chemical structure of the oxidation product; and (c) replacing the oxidized functional group with a carbon-isonitrile functional group to provide a structure of an isonitrile inhibitor of the cytochrome P450.

13. The method of claim 12, wherein the parent compound comprises a steroid or a steroid derivative.

14. The method of claim 12, wherein the oxidized functional group is an alcohol, an aldehyde, a ketone, or a carboxylic acid.

15. The method of claim 12, wherein the parent compound is androsterone and the cytochrome P450 is CYP106A2.

16. A composition comprising:

a plurality of encapsulated nanoparticles, wherein each of the nanoparticles independently comprises a core comprising the compound of claim 1 or a pharmaceutically acceptable salt thereof, and an outer shell at least partially encapsulating the core.

17. The compound of claim 1, wherein the compound is compound 6b.

18. The compound of claim 1, wherein the compound is compound 3a.

19. The compound of claim 1, wherein the compound is compound 3b.

20. The compound of claim 1, wherein the compound is compound 11a.

21. The compound of claim 1, wherein the compound is compound 11b.

22. The compound of claim 1, wherein the compound is compound 11c.

23. The compound of claim 1, wherein the compound is compound 6c.

* * * * *